US008997588B2

(12) United States Patent
Taylor

(10) Patent No.: US 8,997,588 B2
(45) Date of Patent: Apr. 7, 2015

(54) FORCE DETECTING MAT WITH MULTIPLE SENSOR TYPES

(71) Applicant: Stryker Corporation, Kalamazoo, MI (US)

(72) Inventor: Geoffrey L. Taylor, Winnipeg (CA)

(73) Assignee: Stryker Corporation, Kalamazoo, MI (US)

( * ) Notice: Subject to any disclaimer, the term of this patent is extended or adjusted under 35 U.S.C. 154(b) by 215 days.

(21) Appl. No.: 13/802,876

(22) Filed: Mar. 14, 2013

(65) Prior Publication Data

US 2014/0090489 A1    Apr. 3, 2014

Related U.S. Application Data

(63) Continuation-in-part of application No. 13/631,981, filed on Sep. 29, 2012, now Pat. No. 8,904,876.

(51) Int. Cl.
*G01L 1/22* (2006.01)
*G01L 3/00* (2006.01)
(Continued)

(52) U.S. Cl.
CPC . *G01L 1/142* (2013.01); *G01L 1/00* (2013.01); *A61G 7/00* (2013.01); *G01L 1/146* (2013.01); *G01L 1/205* (2013.01)

(58) Field of Classification Search
CPC ........... G01L 1/205; G01L 1/228; G01L 1/16; G01L 1/20; A61B 2562/046; A61B 2562/0247; A61B 5/1036; A61B 5/6892
USPC ..................................... 73/862.041–862.046
See application file for complete search history.

(56) References Cited

U.S. PATENT DOCUMENTS 3,818,756 A    6/1974   Barron et al.
3,996,922 A    12/1976  Basham
(Continued)

FOREIGN PATENT DOCUMENTS

EP    0635251    1/1995
GB    2332063    6/1999
(Continued)

OTHER PUBLICATIONS

J.C. Barbenal et al., "Monitoring the mobility of patients in bed", Medical and Biological Engineering and Computing, pp. 466-468, Sep. 1985.

(Continued)

*Primary Examiner* — Lisa Caputo
*Assistant Examiner* — Jonathan Dunlap
(74) *Attorney, Agent, or Firm* — Warner Norcross & Judd LLP

(57) ABSTRACT

A flexible force or pressure sensing mat includes a first sheet of electrically conductive first paths, a second sheet of electrically conductive second paths, and a sensing layer positioned between the first and second sheets. The first and second conductive paths are oriented transversely to each other, and the locations of their intersections define individual sensing areas or sensors. The sensing layer is made from materials that have first and second electrical characteristics—such as capacitance and resistance—that vary in response to physical forces exerted thereon. A controller repetitively measures the multiple electrical characteristics of each sensor in order to produce a near real time pressure distribution map of the forces sensed by the mat. The mat can be used on a patient support surface—such as a bed, cot, stretcher, recliner, operating table, etc.—to monitor and help reduce the likelihood of a patient developing pressure ulcers.

20 Claims, 26 Drawing Sheets

(51) Int. Cl.
- *G01D 7/00* (2006.01)
- *G01L 1/14* (2006.01)
- *G01L 1/00* (2006.01)
- *A61G 7/00* (2006.01)
- *G01L 1/20* (2006.01)

(56) References Cited

U.S. PATENT DOCUMENTS

| | | |
|---|---|---|
| 4,033,332 A | 7/1977 | Hardway, Jr. et al. |
| 4,267,728 A | 5/1981 | Manley et al. |
| 4,308,872 A | 1/1982 | Watson et al. |
| 4,438,771 A | 3/1984 | Friesen et al. |
| 4,509,527 A | 4/1985 | Fraden |
| RE32,180 E | 6/1986 | Lewiner et al. |
| 4,633,237 A | 12/1986 | Tucknott et al. |
| 4,644,801 A | 2/1987 | Kustanovich |
| 4,657,026 A | 4/1987 | Tagg |
| 4,738,266 A | 4/1988 | Thatcher |
| 4,827,763 A | 5/1989 | Bourland et al. |
| 4,986,277 A | 1/1991 | Sackner |
| 5,002,060 A | 3/1991 | Nedivi |
| 5,010,772 A | 4/1991 | Bourland et al. |
| 5,025,795 A | 6/1991 | Kunig |
| 5,060,174 A | 10/1991 | Gross |
| 5,062,169 A | 11/1991 | Kennedy et al. |
| 5,079,949 A | 1/1992 | Tamori |
| 5,128,880 A | 7/1992 | White |
| 5,178,151 A | 1/1993 | Sackner |
| 5,184,112 A | 2/1993 | Gusakov |
| 5,209,126 A | 5/1993 | Grahn |
| 5,253,656 A | 10/1993 | Rincoe et al. |
| 5,276,432 A | 1/1994 | Travis |
| 5,448,996 A | 9/1995 | Bellin et al. |
| 5,471,198 A | 11/1995 | Newham |
| 5,479,932 A | 1/1996 | Higgins et al. |
| 5,515,738 A | 5/1996 | Tamori |
| 5,571,142 A | 11/1996 | Brown et al. |
| 5,571,973 A | 11/1996 | Taylot |
| 5,590,650 A | 1/1997 | Genova |
| 5,600,108 A | 2/1997 | Newham |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,684,460 A | 11/1997 | Scanlon |
| 5,722,287 A | 3/1998 | Forstein |
| 5,800,360 A | 9/1998 | Kisner et al. |
| 5,800,480 A | 9/1998 | Augustine et al. |
| 5,865,755 A | 2/1999 | Golub |
| 5,964,720 A | 10/1999 | Pelz |
| 5,967,979 A | 10/1999 | Taylor et al. |
| 5,993,400 A | 11/1999 | Rincoe et al. |
| 6,011,477 A | 1/2000 | Teodorescu et al. |
| 6,025,782 A | 2/2000 | Newham |
| 6,033,432 A | 3/2000 | Augustine et al. |
| 6,047,203 A | 4/2000 | Sackner et al. |
| 6,147,592 A | 11/2000 | Ulrich et al. |
| 6,155,120 A | 12/2000 | Taylor |
| 6,180,893 B1 | 1/2001 | Salgo |
| 6,210,427 B1 | 4/2001 | Augustine et al. |
| 6,216,545 B1 | 4/2001 | Taylor |
| 6,279,183 B1 | 8/2001 | Kummer et al. |
| 6,280,392 B1 | 8/2001 | Yoshimi et al. |
| 6,297,738 B1 | 10/2001 | Newham |
| 6,307,168 B1 | 10/2001 | Newham |
| D451,604 S | 12/2001 | Kasabach et al. |
| 6,341,504 B1 | 1/2002 | Istook |
| 6,377,177 B1 | 4/2002 | Broussard et al. |
| 6,387,542 B1 | 5/2002 | Kozlov et al. |
| 6,396,004 B2 | 5/2002 | Salgo |
| 6,413,225 B1 | 7/2002 | Sackner et al. |
| 6,447,457 B1 | 9/2002 | Forstner et al. |
| 6,450,957 B1 | 9/2002 | Yoshimi et al. |
| 6,468,234 B1 | 10/2002 | Van der Loos et al. |
| 6,478,744 B2 | 11/2002 | Mohler |
| 6,485,441 B2 | 11/2002 | Woodward |
| 6,491,647 B1 | 12/2002 | Bridger et al. |
| 6,493,568 B1 | 12/2002 | Bell et al. |
| 6,497,720 B1 | 12/2002 | Augustine et al. |
| 6,498,652 B1 | 12/2002 | Varshneya et al. |
| 6,524,239 B1 | 2/2003 | Reed et al. |
| 6,543,299 B2 | 4/2003 | Taylor |
| 6,546,813 B2 | 4/2003 | Hubbard, Jr. |
| 6,547,743 B2 | 4/2003 | Brydon |
| 6,551,251 B2 | 4/2003 | Zuckerwar et al. |
| 6,551,252 B2 | 4/2003 | Sackner et al. |
| 6,577,897 B1 | 6/2003 | Shurubura et al. |
| 6,585,328 B1 | 7/2003 | Oexman et al. |
| 6,647,289 B2 | 11/2003 | Prutchi |
| 6,684,418 B2 | 2/2004 | Choi |
| 6,685,635 B2 | 2/2004 | Shani et al. |
| 6,698,046 B1 | 3/2004 | Wu |
| 6,721,980 B1 | 4/2004 | Price et al. |
| 6,829,501 B2 | 12/2004 | Nielsen et al. |
| 6,840,117 B2 | 1/2005 | Hubbard, Jr. |
| 6,840,907 B1 | 1/2005 | Brydon |
| 6,853,306 B1 | 2/2005 | Nitschke et al. |
| 6,921,365 B2 | 7/2005 | Lee |
| 6,932,774 B2 | 8/2005 | Nakatani et al. |
| 7,001,334 B2 | 2/2006 | Reed et al. |
| 7,030,764 B2 | 4/2006 | Smith et al. |
| 7,054,679 B2 | 5/2006 | Hirsh |
| 7,065,396 B2 | 6/2006 | Hampton |
| 7,076,371 B2 | 7/2006 | Fu |
| 7,125,383 B2 | 10/2006 | Hoctor et al. |
| 7,155,273 B2 | 12/2006 | Taylor |
| 7,155,281 B1 | 12/2006 | Fayram |
| 7,173,437 B2 | 2/2007 | Hervieux et al. |
| 7,201,063 B2 | 4/2007 | Taylor |
| 7,204,808 B1 | 4/2007 | Friedman et al. |
| 7,211,053 B2 | 5/2007 | Marmaropoulos et al. |
| 7,245,956 B2 | 7/2007 | Matthews et al. |
| 7,282,654 B2 | 10/2007 | Salgo et al. |
| 7,319,386 B2 | 1/2008 | Collins, Jr. et al. |
| 7,330,127 B2 | 2/2008 | Price et al. |
| 7,365,031 B2 | 4/2008 | Swallow et al. |
| 7,437,787 B2 | 10/2008 | Bhai |
| 7,459,645 B2 | 12/2008 | Skinner et al. |
| 7,480,953 B2 | 1/2009 | Romano et al. |
| 7,500,280 B2 | 3/2009 | Dixon et al. |
| 7,515,059 B2 | 4/2009 | Price et al. |
| 7,557,718 B2 | 7/2009 | Petrosenko et al. |
| 7,568,246 B2 | 8/2009 | Weismiller et al. |
| 7,631,557 B2 | 12/2009 | DeBeliso et al. |
| 7,646,294 B2 | 1/2010 | Kow et al. |
| 7,656,299 B2 | 2/2010 | Gentry et al. |
| 7,657,956 B2 | 2/2010 | Stacy et al. |
| 7,699,784 B2 | 4/2010 | Wan Fong et al. |
| 8,161,826 B1 | 4/2012 | Taylor |
| 2001/0042412 A1 | 11/2001 | Serban et al. |
| 2002/0194934 A1 | 12/2002 | Taylor |
| 2003/0004423 A1 | 1/2003 | Lavie et al. |
| 2004/0087865 A1 | 5/2004 | Kelly |
| 2004/0167418 A1 | 8/2004 | Nguyen et al. |
| 2004/0186380 A1 | 9/2004 | Kristiansen |
| 2004/0210155 A1 | 10/2004 | Takemura et al. |
| 2005/0075542 A1 | 4/2005 | Goldreich |
| 2005/0101875 A1 | 5/2005 | Semler et al. |
| 2005/0124864 A1 | 6/2005 | Mack et al. |
| 2005/0171443 A1 | 8/2005 | Gorenberg et al. |
| 2005/0190068 A1 | 9/2005 | Gentry et al. |
| 2005/0241409 A1 | 11/2005 | Taylor |
| 2005/0245839 A1 | 11/2005 | Stivoric et al. |
| 2005/0268962 A1 | 12/2005 | Gaudiana et al. |
| 2006/0028350 A1 | 2/2006 | Bhai |
| 2006/0065060 A1 | 3/2006 | Ito et al. |
| 2006/0066449 A1 | 3/2006 | Johnson |
| 2006/0100530 A1 | 5/2006 | Kliot et al. |
| 2006/0100534 A1 | 5/2006 | Colombo et al. |
| 2006/0129047 A1 | 6/2006 | Ruotoistenmaki |
| 2006/0162464 A1 | 7/2006 | Hayashi et al. |
| 2006/0173363 A1 | 8/2006 | Felder et al. |
| 2006/0195035 A1 | 8/2006 | Sun |
| 2006/0224072 A1 | 10/2006 | Shennib |

(56) References Cited

U.S. PATENT DOCUMENTS

| | | |
|---|---|---|
| 2006/0224076 A1 | 10/2006 | Lange et al. |
| 2006/0241510 A1 | 10/2006 | Halperin et al. |
| 2006/0258914 A1 | 11/2006 | Derchak et al. |
| 2006/0260417 A1 | 11/2006 | Son et al. |
| 2006/0264767 A1 | 11/2006 | Shennib |
| 2007/0083096 A1 | 4/2007 | Paradiso |
| 2007/0118054 A1 | 5/2007 | Pinhas et al. |
| 2007/0125181 A1 | 6/2007 | Ofek et al. |
| 2007/0149883 A1 | 6/2007 | Yesha |
| 2007/0156031 A1 | 7/2007 | Sullivan et al. |
| 2008/0200085 A1 | 8/2008 | Van Bruggen et al. |
| 2008/0229839 A1 | 9/2008 | Chakraborty |
| 2009/0056020 A1 | 3/2009 | Caminade et al. |
| 2009/0056027 A1 | 3/2009 | Ball et al. |
| 2009/0093990 A1 | 4/2009 | McGuire et al. |
| 2009/0099480 A1 | 4/2009 | Salgo et al. |
| 2009/0183312 A1 | 7/2009 | Price et al. |
| 2010/0045454 A1 | 2/2010 | Knight et al. |
| 2010/0094139 A1 | 4/2010 | Brauers et al. |
| 2010/0095462 A1 | 4/2010 | Bobey et al. |
| 2010/0308846 A1 | 12/2010 | Camus |
| 2011/0068939 A1 | 3/2011 | Lachenbruch |
| 2012/0055257 A1 | 3/2012 | Shaw-Klein |
| 2012/0116251 A1 | 5/2012 | Ben-Shalom et al. |
| 2012/0234105 A1 | 9/2012 | Taylor |
| 2013/0091961 A1 | 4/2013 | Taylor |

FOREIGN PATENT DOCUMENTS

| | | |
|---|---|---|
| JP | 2000000214 | 1/2000 |
| JP | 2000175904 A | 6/2000 |
| JP | 20000316915 A | 11/2000 |
| JP | 2001000401 A | 1/2001 |
| JP | 2001037821 A | 2/2001 |
| JP | 2004180804 | 7/2004 |
| JP | 2005013259 | 1/2005 |
| JP | 2005204930 | 8/2005 |
| JP | 2005218604 | 8/2005 |
| JP | 2008049023 | 3/2008 |
| WO | 2005000108 | 1/2005 |
| WO | 2005104904 | 11/2005 |
| WO | 2009013981 | 1/2009 |
| WO | 2009120270 | 10/2009 |
| WO | 2012122002 | 9/2012 |

OTHER PUBLICATIONS

Charles F. Babbs, et al., "A Pressure-Sensitive Mat for Measuring Contact Pressure Distributions . . . ", Biomedical Instrumentation and Technology, pp. 363-370, Sep./Oct. 1990.

Makoto Shimojo, et al., A Tactile Sensor Sheet Using Pressure Conductive Rubber With Electrical-Wires Stitched Method, IEEE Sensors Journal, vol. 4, No. 5, Oct. 2004.

Apr. 5, 2010 Webpages from www.swicofil.com/textile_metallization.html.

Laird Technologies. Nick/Copper Polyester Taffeta. Product Specification for 3035-213. <Accessed Online> Sep. 6, 2011. <http://www.stockwell.com/data_sheets/esd_emi/3035213_nickel_polyester_taffeta.pdf>.

Bergen Cable Technology. Cabel 101. <Accessed Online> Sep. 7, 2011. <http://www.bergencable.com/technology/technology_cable101.html>.

PCT International Search Report regarding Application No. PCT/US2013/062071 filed Sep. 27, 2013, a counterpart of U.S. Appl. No. 13/802,876.

PCT International Written Opinion regarding Application No. PCT/US2013/062071 filed Sep. 27, 2013, a counterpart of U.S. Appl. No. 13/802,876.

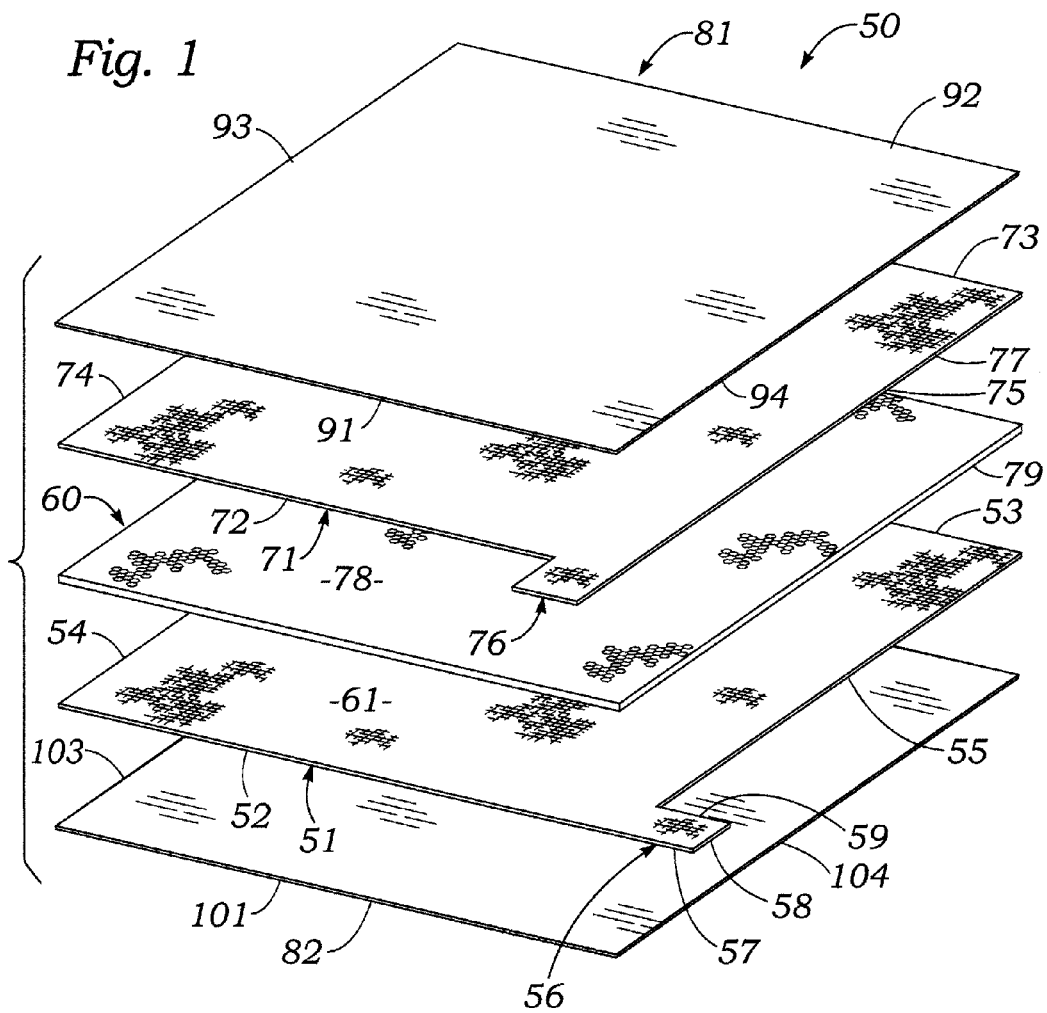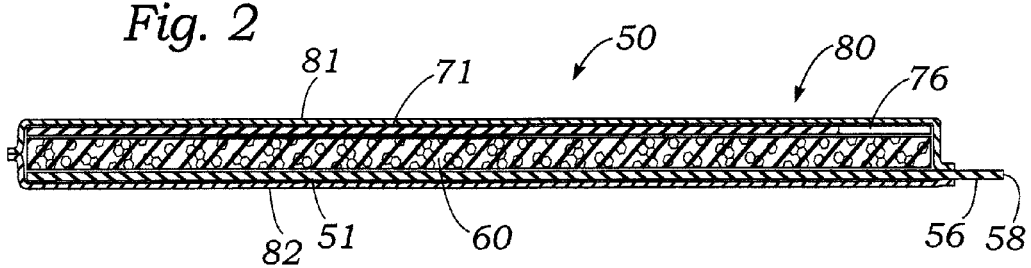

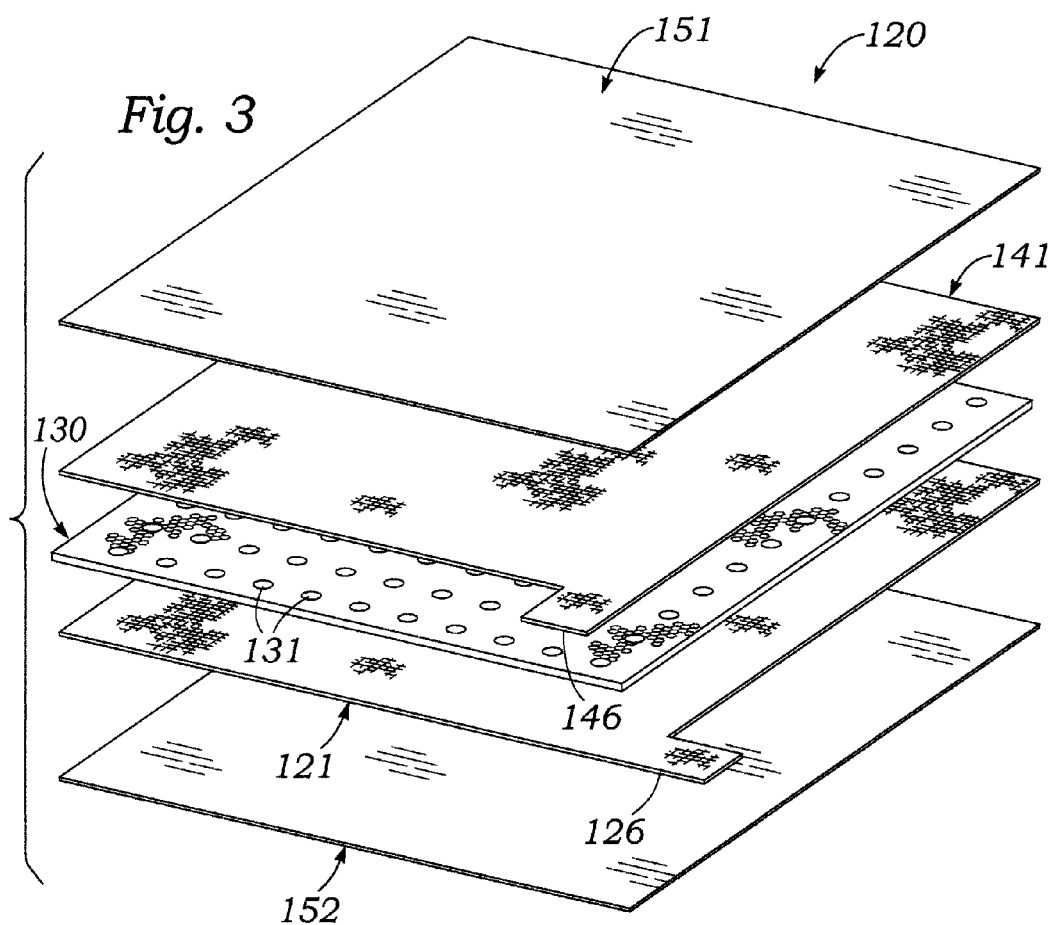
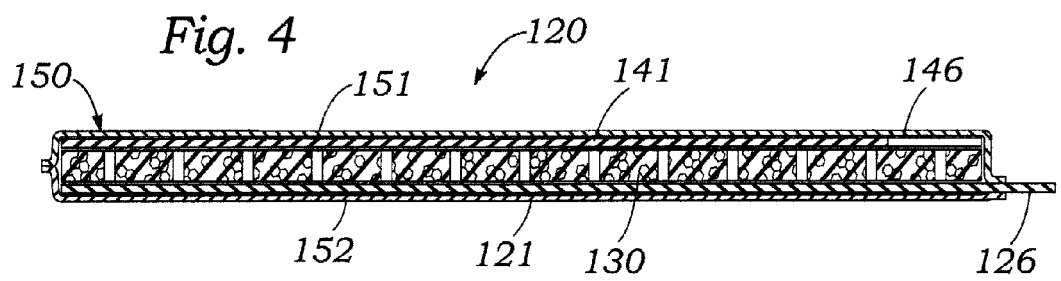

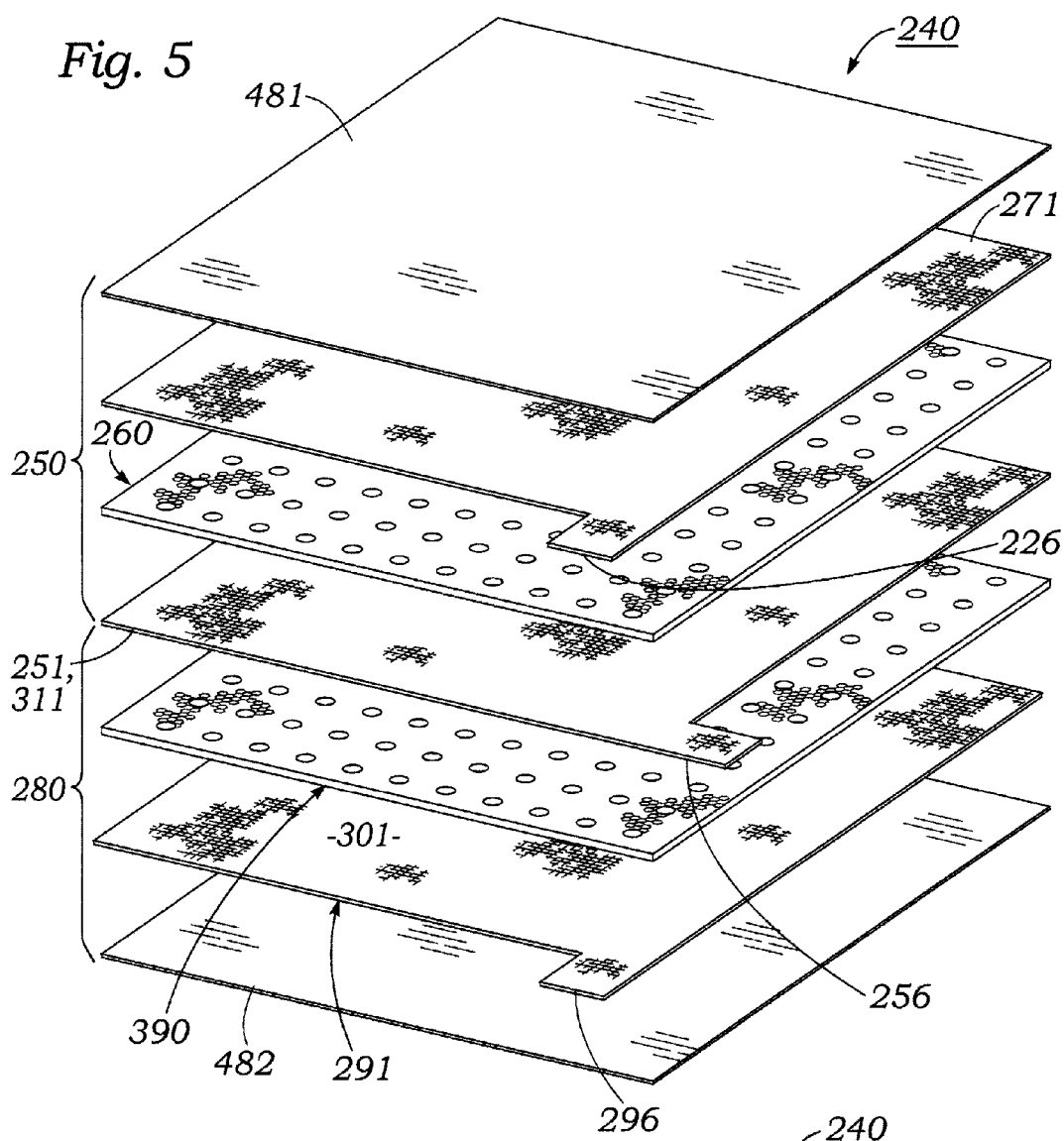
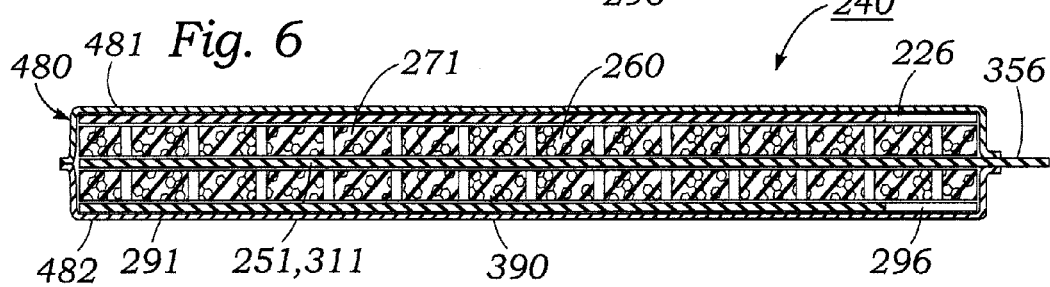

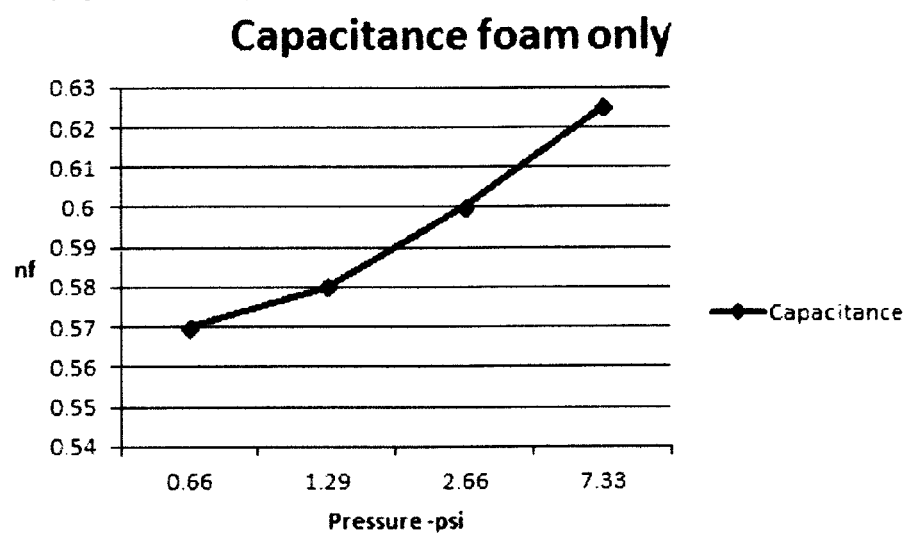
Fig 10A Capacitance vs Pressure Example 1 (Figures 1 & 2)

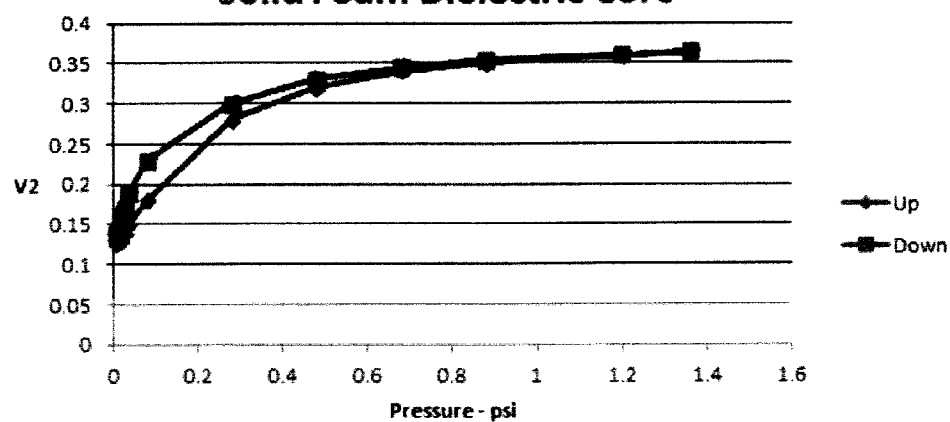

Fig 11 A  Capacitance vs Pressure of Perforated Foam Sensor Example 2 (Figure 3 & 4) 50% holes in foam core
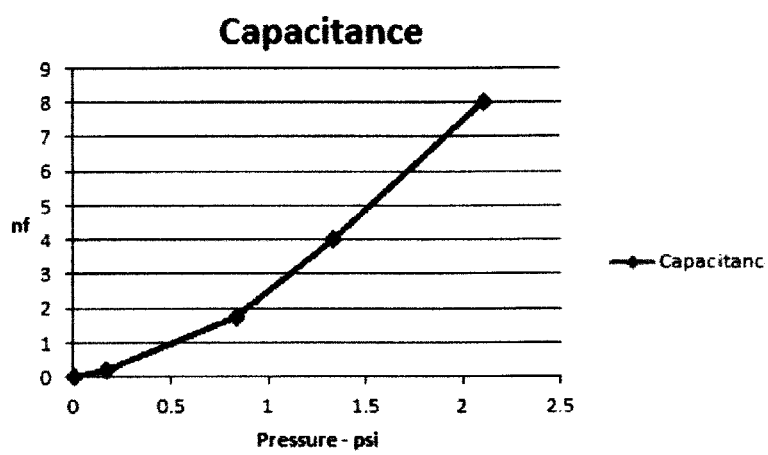

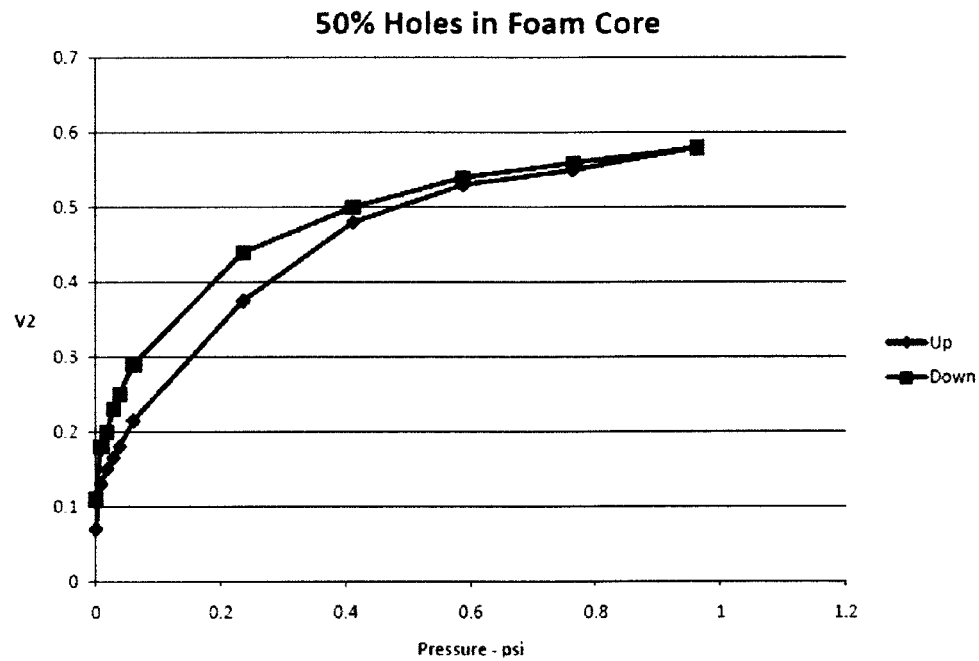
Fig 11B Susceptance vs Pressure of Perforated Foam Sensor Example 2 (Figures 3 & 4)

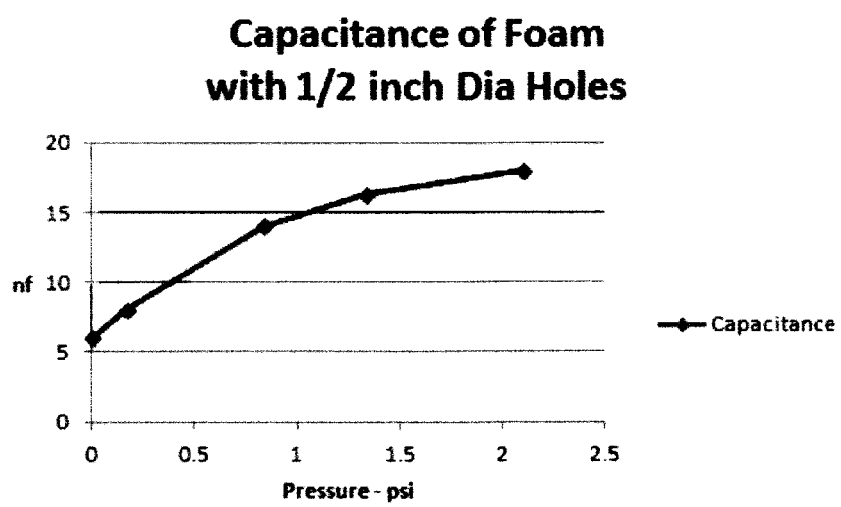
Fig 12 Capacitance vs Pressure of Perforated Foam Sensor Saturated with Glycerin (Example 3, Figures 3 & 4)

Fig 13  Capacitance vs Pressure of Perforated Foam saturated with Glycerin and Iodine (Example 4, Figures 3 & 4)
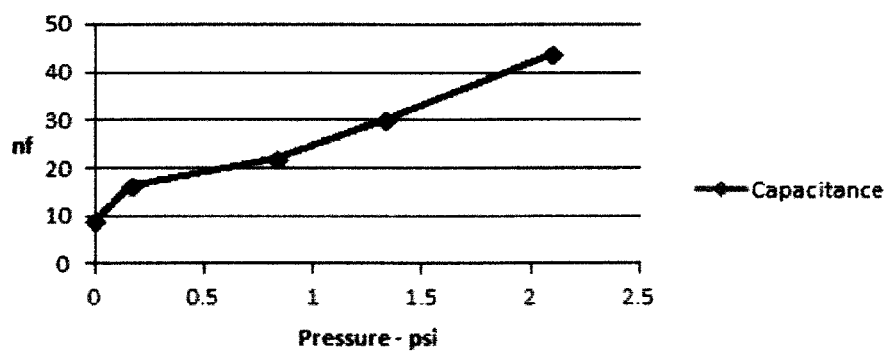

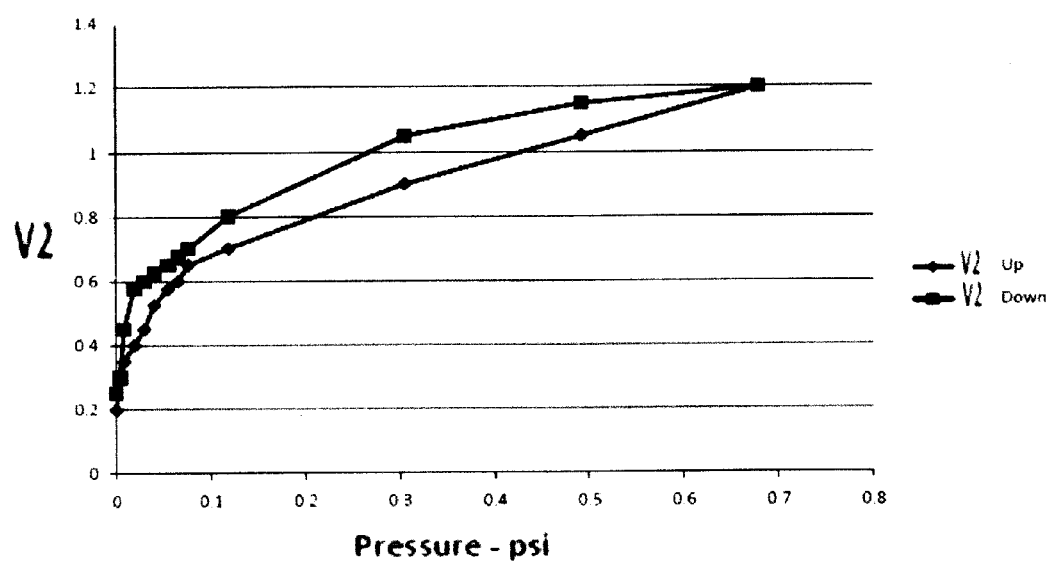
Fig 14 Susceptance vs Pressure of Composite on Hbrid Sensor Example 5 (Figures 5 & 6) Measured @ 30 KHz

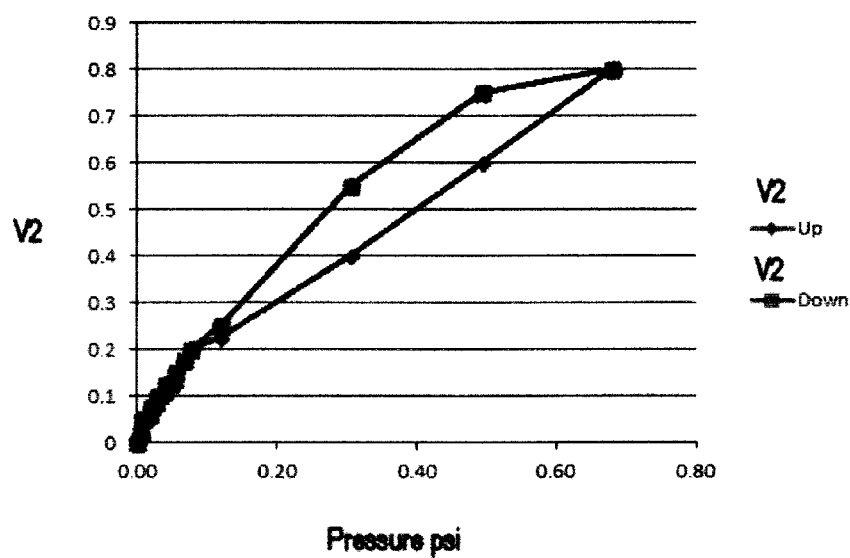
Fig 15. Conductance vs Pressure for Composite or Hybrid Sensor of Example 5 (Figures 5 & 6) Measured @ 10Hz

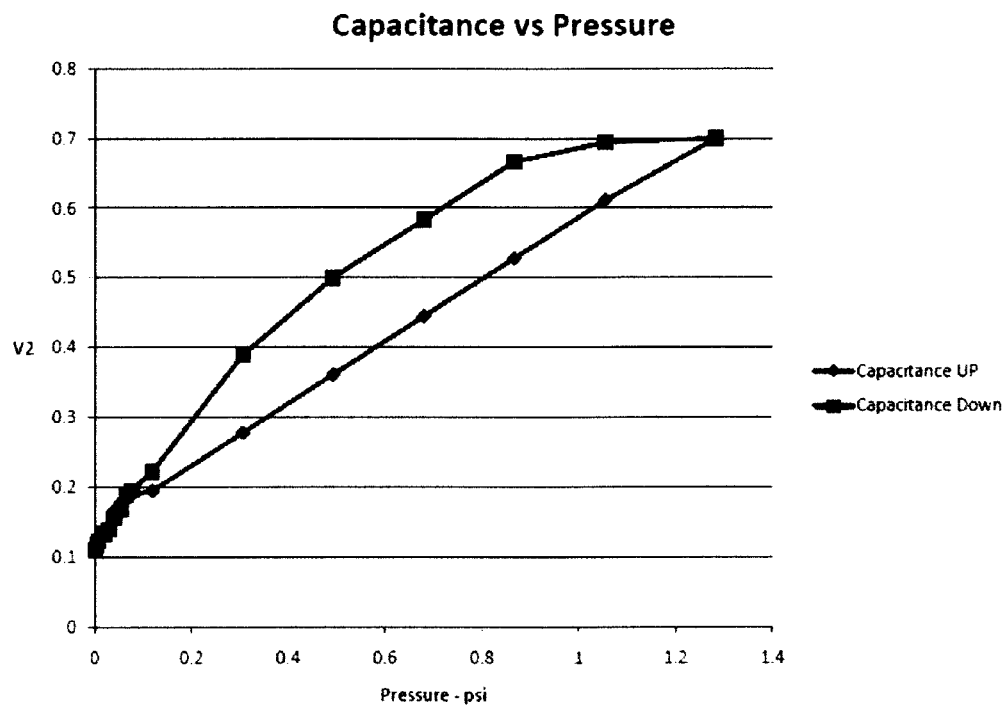
Fig 16 Susceptance vs Pressure of Leaky Dielectric Sensor Example 6 (Figures 7 & 8) measured @ 30KHz

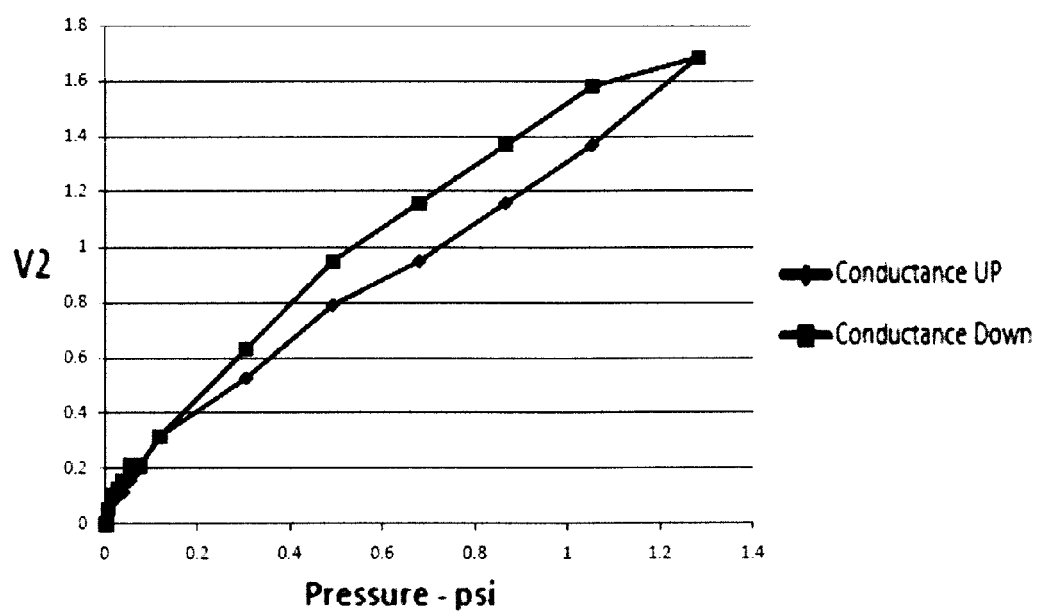

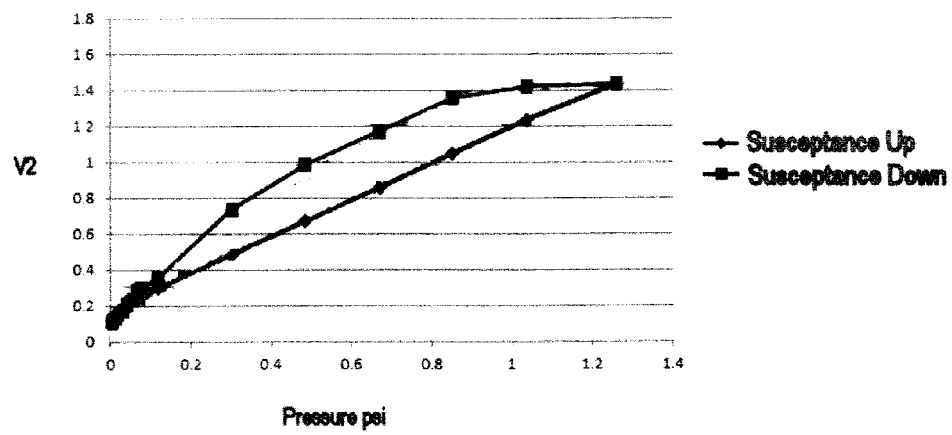
Fig 18 A  Susceptance vs Pressure of Leaky Dielectric Sensor
Example 6  (Figures 7 & 8)
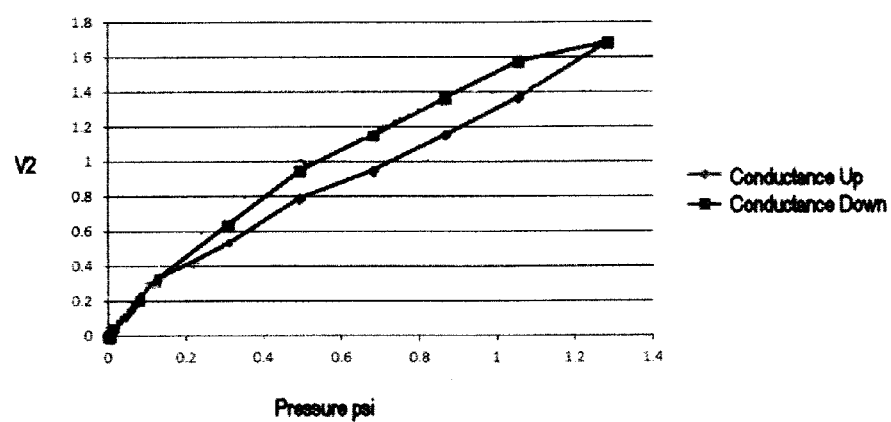
Fig 18 B  Conductance vs Pressure of Leaky Dielectric Sensor
Example 6  (Figures 7 & 8)

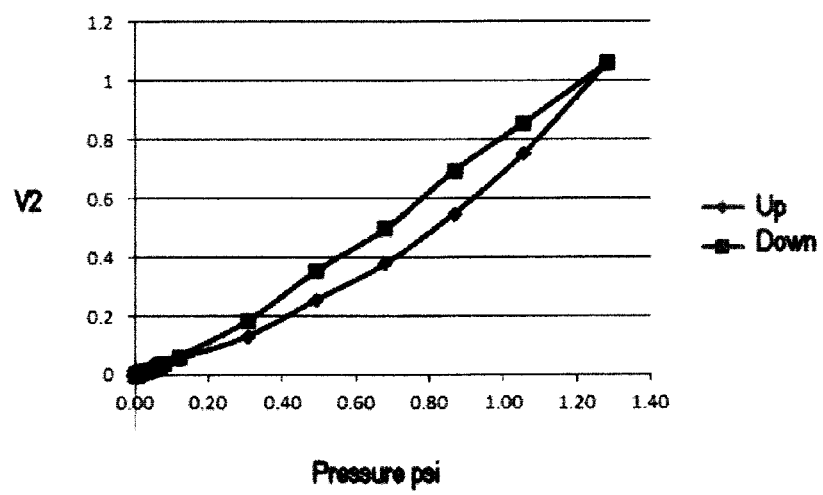
Fig 19  Susceptance times Conductance as a function of pressure
of Leaky Dielectric Sensor
Example 6  (Figures 7 & 8)

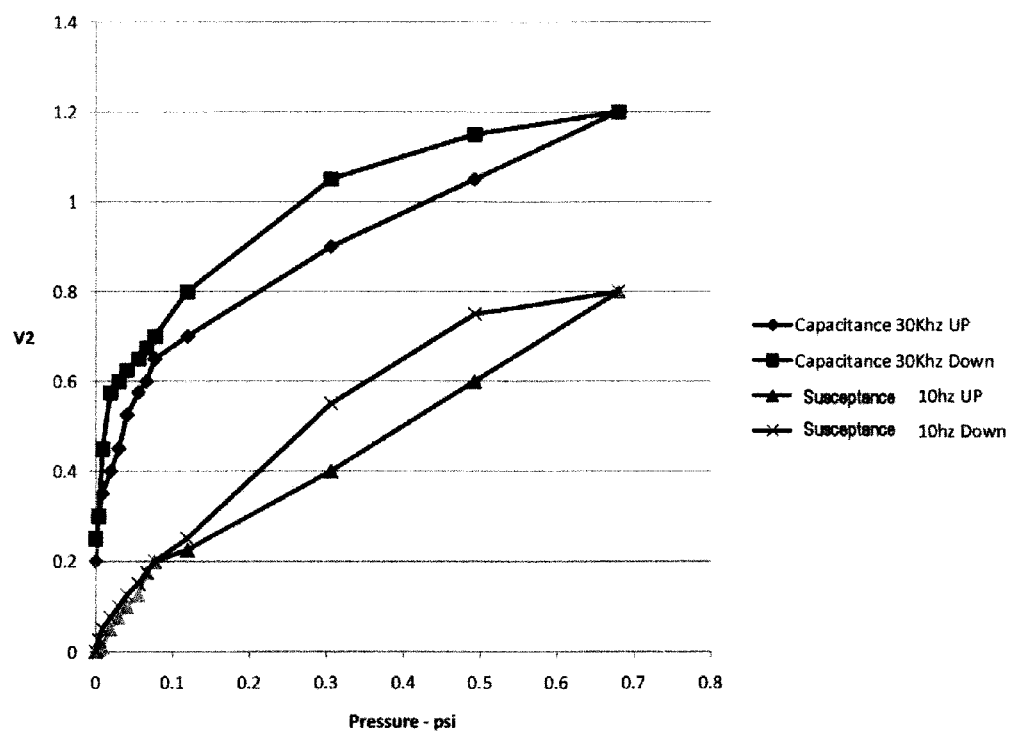

Fig 21   Conductance vs Pressure of Hybrid Sensor
With 10Kohm Resister in Series
Example 8 (Figures 5 & 6)
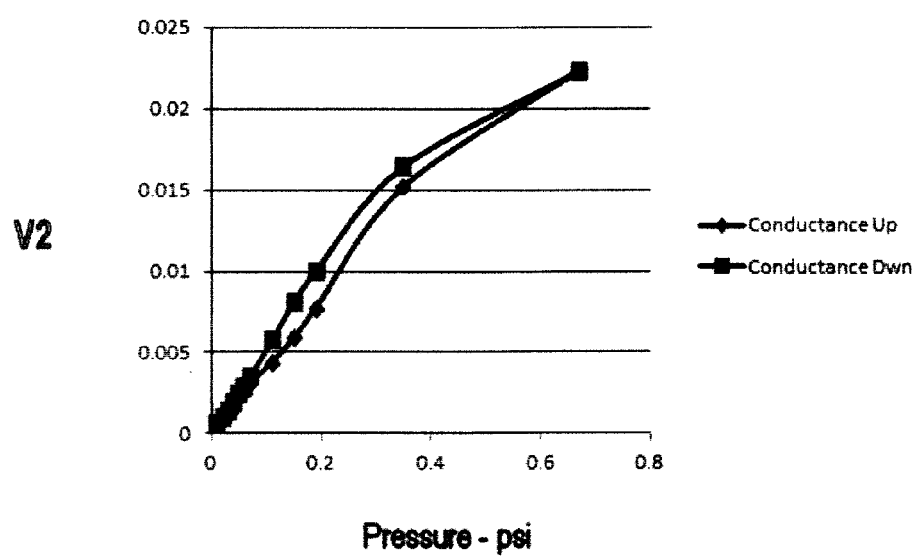

Fig 24 Susceptance of Simplified Leaky Dielectric Sensor Example 9 (Figures 22 & 23)

Fig 26 Conductance vs Pressure of Simplified Leaky Dielectric Sensor Example 9 (Figures 22 & 23)

Ref Table 13

Fig 27   Conductance times susceptance of Simplified Leaky Dielectric Sensor Example 9 Figures 22 & 23)

Ref Table 14        Pressure psi

FORCE DETECTING MAT WITH MULTIPLE SENSOR TYPES

CROSS-REFERENCE TO RELATED APPLICATIONS

This application is a continuation-in-part of U.S. patent application Ser. No. 13/631,981 filed Sep. 29, 2012 by applicants Geoffrey Taylor et al., entitled FLEXIBLE PIEZOCAPACITIVE AND PIEZORESISTIVE FORCE AND PRESSURE SENSORS.

BACKGROUND OF THE INVENTION

The present invention relates to sensors for measuring forces or pressures exerted thereon, and more particularly to a sensing mat that can be used to monitor interface pressures between a person and a surface.

Force sensing mats may be used to detect interface pressures between a patient and a surface on which he or she is lying or sitting. In a healthcare setting, the surface may be the top surface of a patient support device—such as a hospital bed, stretcher, cot, chair, or the like—or it may be another type of surface. Knowing these interface pressures can be useful for helping to prevent and/or treat pressure sores, as well as for other purposes.

SUMMARY OF THE INVENTION

The present invention provides a flexible, dual sensor force detecting mat or array that is adapted to detect interface forces exerted between a person and a support surface, as well as between any other forces that may be exerted on the force detecting mat or array. The mat or array utilizes a combination of at least two different sensing technologies that, in combination, provide more information that a single sensing technology. Such additional information can be useful for a variety of purposes, such as, but not limited to, improving the dynamic range of the forces that are able to be sensed by the sensing mat. In one embodiment, the two different sensing technologies include piezoresistive sensors and piezocapacitive sensors.

According to a first embodiment, a flexible force sensing mat is provided that includes a first sheet, a second sheet, a layer of sensing material, and a controller. The first sheet has a plurality of first conductive paths supported thereon and the second sheet has a plurality of second conductive paths supported thereon. The layer of sensing material is positioned in contact with, and between, the conductive paths on the first and second sheets. The layer of sensing material has first and second electrical characteristics that vary in response to physical forces exerted thereon. The second plurality of conductive paths on the second sheet are oriented transverse to the plurality of first conductive paths on the first sheet. The controller is adapted to detect changes in both the first and second electrical characteristics when force is applied to the force sensing mat.

According to a second embodiment, a flexible force sensing mat is provided that includes first, second, and third sheets, and first and second layers of sensing material. The first sheet includes a plurality of first conductive paths supported thereon. The first layer of sensing material is positioned in contact with the first conductive paths and has a first electrical characteristic that varies in response to physical forces exerted thereon. The second sheet includes a plurality of second conductive paths supported thereon. The second sheet is positioned in contact with the first layer of sensing material on a side of the layer of sensing material opposite the first sheet. The second layer of sensing material is in contact with the plurality of second conductive paths and has a second electrical characteristic that varies in response to physical forces exerted thereon. The second electrical characteristic is different from the first electrical characteristic. The third sheet includes a plurality of third conductive paths supported thereon and the third sheet is positioned in contact with the second layer of sensing material on a side of the second layer of sensing material opposite the second sheet.

According to other embodiments, the first sheet, second sheet, and layer or layers of sensing material are elastically stretchable in at least two co-planar and orthogonal directions. The first, second, and/or third sheets may be made of nylon. The conductive paths may be defined by metal plated to the respective sheets.

In some embodiments, the first electrical characteristic is capacitance and the second electrical characteristic is resistance. The detection of the first and second electrical characteristics may be accomplished by feeding first and second signals to the conductive paths wherein the first and second signals have different frequencies.

In the embodiments where a single layer of sensing material has both the first and second electrical characteristics, the sensing material may include carbon black and glycerin mixed together. The carbon black and glycerin may be supported in a foam pad positioned between the first and second sheets. The glycerin acts as a liquid dielectric which holds in suspension the carbon black, which acts as a piezoresistive substance.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 1 is an exploded perspective view of a first embodiment of a force sensor having a piezocapacitive layer according to one aspect of the invention;

FIG. 2 is a vertical sectional view of the sensor of FIG. 1;

FIG. 3 is an exploded perspective view of a second embodiment of a force sensor in which a central foam dielectric pad thereof is perforated;

FIG. 4 is a vertical sectional view of the sensor of FIG. 3;

FIG. 5 is an exploded perspective view of a third embodiment of a force sensor having a piezocapacitive layer and a separate piezoresistive layer;

FIG. 6 is a vertical sectional view of the sensor of FIG. 5;

FIG. 10A is a graph showing capacitance versus applied pressure for the first sensor embodiment of FIGS. 1 and 2;

FIG. 10B is a graph showing capacitance of the first sensor embodiment of FIGS. 1 and 2 plotted as a function of increasing and decreasing pressure applied to the sensor, using the test circuitry shown in FIG. 9;

FIG. 11A is a graph showing capacitance versus applied pressure for the second sensor embodiment of FIGS. 3 and 4;

FIG. 11B is a graph showing capacitance versus increasing and decreasing pressures for the second sensor embodiment of FIGS. 3 and 4, using the test circuitry shown in FIG. 9;

FIG. 12 is a graph showing capacitance versus applied pressure for a first variation of the second sensor embodiment of FIGS. 3 and 4, filled with glycerin;

FIG. 13 is a graph showing capacitance versus pressure for a second variation of the second sensor embodiment of FIGS. 3 and 4, filled with both glycerin and iodine;

FIG. 14 is a graph showing capacitance versus applied pressure for the third sensor embodiment of FIGS. 5 and 6;

FIG. 15 is a graph showing conductance versus applied pressure for the third sensor embodiment of FIGS. 5 and 6;

FIG. 16 is a graph showing capacitance versus applied pressure for the fourth sensor embodiment of FIGS. 7 and 8;

FIG. 17 is a graph showing conductance versus applied pressure for the fourth sensor embodiment of FIGS. 7 and 8;

FIG. 18A is a graph showing susceptance plotted as a function of applied pressure for the fourth sensor embodiment of FIGS. 7 and 8;

FIG. 18B is a graph showing conductance plotted as a function of applied pressure for the fourth sensor embodiment of FIGS. 7 and 8;

FIG. 19 is a variation of FIG. 18, in which the product of conductance and capacitance for the fourth sensor embodiment of FIGS. 7 and 8 is plotted;

FIG. 20 is a graph showing a plot of capacitance versus applied pressure for a modified configuration of the third sensor embodiment of FIGS. 5 and 6;

FIG. 21 is a graph similar to that of FIG. 20, but with the sensors of FIGS. 5 and 6 modified by insertion of a 10,000 ohm resistor in series with the piezoresistive layer of the sensor;

DETAILED DESCRIPTION OF THE EMBODIMENTS

Figure 7:
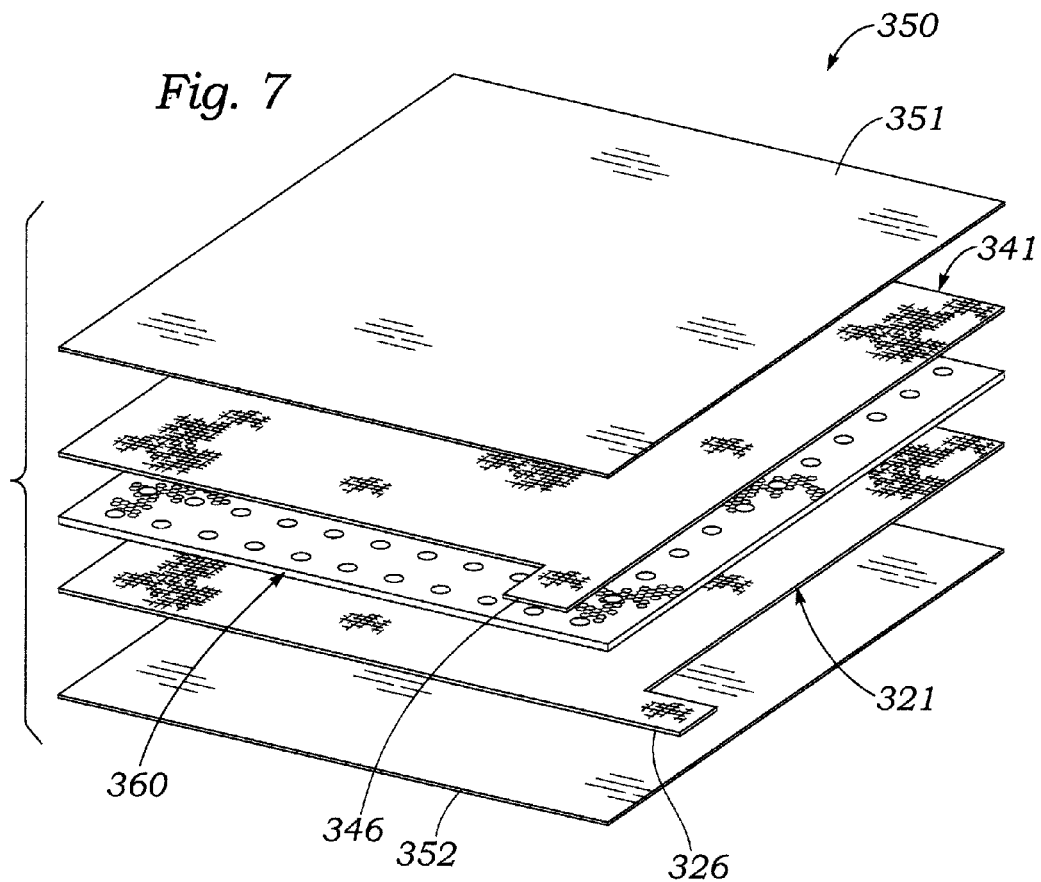
FIG. 7 is an exploded perspective view of a fourth embodiment of a force sensor having a combined layer of piezocapacitive and piezoresistive material.

According to various aspects of the present invention, an individual pressure sensor, or an array of pressure sensors incorporated into a mat, are provided that can be used to measure forces or pressures exerted on individual areas of an object, such as a human body supported by a bed, a chair, a cot, a stretcher, an operating table, or another object. In some embodiments, the pressure sensors, or pressure sensing mats, are designed such that the electrical capacitance of the sensor varies in a repeatable fashion as function of force or pressure applied to the sensor, a property which is referred to as piezocapacitance. This property enables the sensors to measure force or pressure exerted on the sensor by applying an alternating voltage or current to terminals of the sensor and measuring the output current or voltage of the sensor, which varies with force or pressure according to a transfer function that has been previously obtained for the sensor by a calibration procedure in which the impedance of the sensor is measured and recorded for a sequence of known calibrating forces or pressures applied to the sensor.

When the individual sensors are configured into an array of individual sensors, a pressure map can be easily obtained that graphically, or numerically, defines the distribution of pressures exerted on a human body by the object on which the body is supported.

The force sensors, in some embodiments, include both a piezoresistive characteristic and a piezocapacitive characteristic, thus resulting in sensors in which both the DC conductance, as well as the electrical capacitance, vary as a function of applied forces or pressures. The combined variation of conductance and capacitance affords increased versatility to the hybrid sensors, including wider dynamic ranges.

EXAMPLE 1

Referring first to FIGS. 1 and 2, a first embodiment of a piezocapacitive pressure sensor 50 according to one aspect of the present invention is shown that includes a flexible conductive sheet 51 which functions as the first conductive plate of a capacitor. Base conductive sheet 51 is made of a thin, flexible, elastically stretchable fabric which is electrically conductive. In an example embodiment of sensor 50, base conductive sheet consists of a two inch square piece of a elastically stretchable woven electrical conductive fabric made of silver plated nylon threads, having a thickness of 0.4 mm, a weight per unit/area of 4.3 oz. per square yard, and a surface resistance of about 0.5 ohms per square. Such fabric is available from LESS EMF Corporation, 809 Madison Ave., Albany, N.Y. 12208 as catalog or part number A321.

As shown in FIG. 1, base conductor sheet 51 has a front laterally disposed edge 52, a parallel rear laterally disposed edge 53, and left and right parallel fore-and-aft disposed edges 54, 55. Base conductor sheet 51 has an integral rectangular-shaped conductive fabric connector tab 56 which is coplanar with and protrudes perpendicularly outwards from a corner part of the square conductor sheet. Thus, as shown in FIG. 1, base connector tab 56 has a front laterally disposed edge 57 which is a collinear extension of front edge 52 of base conductor sheet 51, an outer fore-and-aft disposed edge 58 parallel to and offset laterally to the right of right-hand edge 55 of the base conductor sheet 51, and a laterally inwardly extending rear edge 59 which is parallel to front edge 57.

Sensor 50 further includes a dielectric pad or core 60 which is supported on the upper surface 61 of base conductor sheet 51 (FIGS. 1 and 2). As shown in the figures, dielectric pad 60 has approximately the same outline shape and size, e.g., a two inch square, as base conductor sheet 51, so that the dielectric pad 60 seats congruently of the base conductor sheet. In an example embodiment of sensor 50, dielectric pad 60 is made of a 2-inch square piece of elastically deformable polyurethane open-cell foam having a thickness of about 0.025 inch. The dielectric pad 60 is cut from a piece of open cell polyurethane foam having a density of about 28.52 kg/cubic meter, obtainable from Burnett and Company, Foam Division, 2112 Montevideo Road, Jussea, Md. 20604, stock number SBZJJ. The dielectric pad 60 has a dielectric constant or relative permittivity of about 4.

Referring to FIG. 1, it may be seen that piezocapacitive sensor 50 has an upper flexible conductive sheet 71 which functions as the second plate of a capacitor. Outer flexible conductive sheet 71 may be substantially identical in construction to base conductive sheet 51. However, as shown in FIG. 1, upper flexible conductive sheet 71 is flipped over and rotated 90 degrees relative to base conductive sheet, so that a connector tab 76 of the upper conductive sheet 71 extends forward from the front edge of sensor 50, so that it does not overlie the rightwardly extending connector tab 56 of base conductive sheet 51.

As shown in FIGS. 1 and 2, upper conductive sheet 71 has a lower flat surface 77 which contacts upper flat surface 78 of dielectric pad 60, and dielectric pad 60 has a lower surface 79 which contacts upper surface 61 of base conductive sheet 51. As shown in FIG. 2, the sandwiched relationship between base conductive sheet 51, dielectric pad 60, and upper conductive sheet 71 is maintained by encapsulating these three elements in a flat flexible envelope 80, thereby restraining these elements from relative movement with respect to each other.

As shown in FIGS. 1 and 2, encapsulating envelope 80 includes upper and lower flexible liquid impervious polyurethane cover sheets 81, 82 made of 2-mil thick polyurethane film. Upper and lower encapsulating polyurethane sheets 81, 82 have a square shape, and are slightly larger in area than upper conductive sheet 71, dielectric pad 60 and base conductive sheet 51. This size relationship enables front, rear, left and right outer peripheral edges 91, 92, 93, 94 of upper encapsulating cover sheet 81 to be sealingly joined by adhesive, ultrasonic bonding, or other suitable techniques to corresponding outer peripheral edges 101, 102, 103, 104 of lower encapsulating cover sheet 82.

Figure 9:
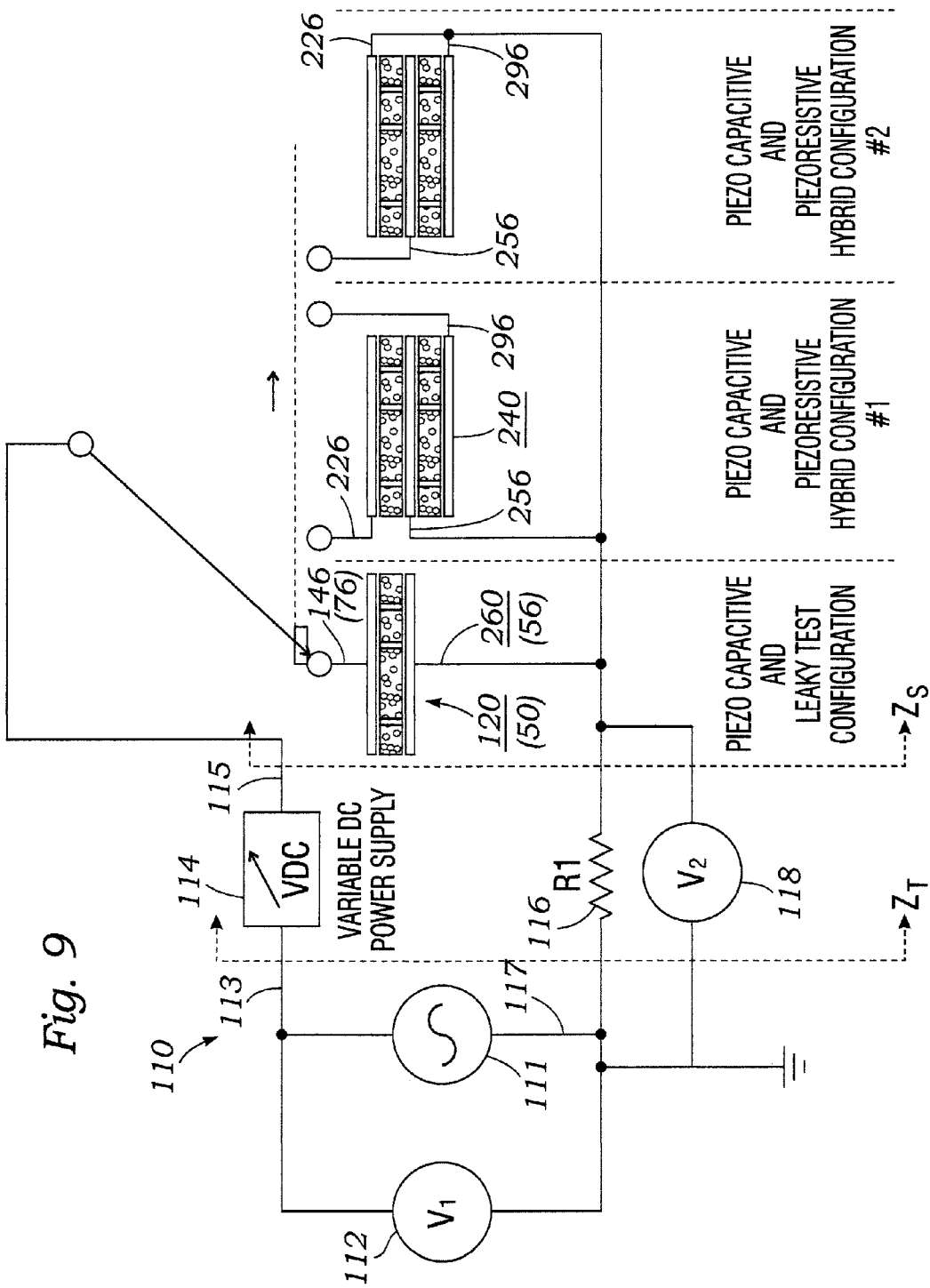
FIG. 9 is a schematic diagram of an apparatus useable both for determining transfer functions of the sensors shown in FIGS. 1-8, and for measuring pressure exerted on the sensors.

FIG. 9 is a schematic diagram of a pressure measurement apparatus 110 according to another aspect of the present invention, showing how the sensor of FIGS. 1 and 2 can be connected to test circuitry to measure how its capacitance, conductance, or admittance changes in response to external pressure exerted on the sensor. From these measurements the transfer function of the sensor may be plotted. The apparatus of FIG. 9 is also useable to measure forces or pressures exerted on sensors 50 for which the impedance-versus-force transfer function has been previously determined.

As shown in FIG. 9, apparatus 110 includes a selectable frequency signal generator 111 which outputs a sinusoidal current that is adjustable to a selectable voltage V1, measured by a voltmeter 112. Signal generator 111 has connected in series with output terminal 113 thereof a variable voltage DC power supply 114 which outputs a voltage selectable between zero and a predetermined maximum value. The output terminal 115 of DC power supply 114 is connected to one terminal, e.g., upper connector tab 76 of sensor 50. The opposite terminal, e.g. lower connector tab 56 of the sensor 50 is connected through a current sampling resistor 116 to the lower or ground output terminal 117 of signal generator 111.

Current flowing through sensor 50 in response to a DC voltage, an AC voltage, or a combination of both AC and DC voltages applied to terminals 76-56 of the sensor, is measured by measuring the voltage drop V2 across resistor 116 using a voltmeter 118. Thus the DC conductance of sensor 50 may be measured by applying a DC voltage or low-frequency AC signal to the sensor. The AC conductance or susceptance, which is proportional to capacitance, may be measured by applying a higher frequency test voltage to the terminals of sensor 50, or, alternatively, by substituting a capacitance meter or bridge for the signal generator 111.

FIG. 10A is a graph showing the variation of capacitance of sensor 50 of FIGS. 1 and 2 as a function of increasing applied pressure, as measured by a capacitance meter.

Referring to FIG. 9, the total impedance seen by signal generator 111 is:

$$Z1 = R1^2 + Zs^2$$

where $$Zs = Rs^2 + Xs^2$$

and Rs is the resistive component of sensor impedance Zs, and Xs is the capacitive reactive component of sensor impedance Zs. In other words, Xs=½πrfCs where f is the signal generator frequency and Cs is the capacitance of the sensor. The current Is through sampling resistor R1 and sensor 50 is:

Is=V1/Z1, and for R1 selected to be much smaller than Zs, Is=V1/Zs.

For the capacitance component of sensor impedance, Zs, Is=V1×Bs, where Bs is the susceptance of the capacitive component of the sensor, Bs=2πfCs.

For the resistive component of sensor impedance Zs, Is=V1/Gs, where Gs is the DC conductance of the sensor.

Referring to FIG. 9,

V2=Is R1=V1(2π)fCsR1 for the capacitance component of a sensor, and

V2=IsR1=V1GsR1 for the resistive component. Thus, the capacitance of a sensor may be calculated from the equation: Cs=(V2/V1)(2πrfR1), or Cs=k1(V2/V1); for f=30 KHz and R1=1,000 ohm, k1=5.305×10⁻⁹ farads=5.305 nanofarads, and for V1=9 volts, Cs=kc×V2=0.5895 of/volt.

For the resistance component of sensor 50, Gs=V2/V1, R1=1,000 ohms, V1=9 volts;

Gs=kg (V2)=0.1111 millimhos/volt.

FIG. 10B is a graph which plots the transfer function of the sensor 50 of FIGS. 1 and 2.

EXAMPLE 2

Perforated Pad

FIGS. 3 and 4 illustrate a modified sensor 120 according to another embodiment that has been modified from the sensor 50 shown in FIGS. 1 and 2. Modified sensor 120 is substantially similar in construction and function to sensor 50, with the primary difference being that the central dielectric pad 130 of sensor 120 contains perforations. In an example embodiment of sensor 120, central dielectric pad 130 has an array of circular holes 131 defined through the thickness dimension of the pad and spread over the entire area of pad 130. Each hole has a diameter of ½ inch and is spaced apart by ¼ inch from adjacent holes. The holes 131 occupy about fifty percent of the surface area of the pads.

FIG. 11 A is a plot of capacitance versus applied pressure for sensor 120 shown in FIGS. 3 and 4.

FIG. 11 B shows the variation of voltage ratios V2/V1 proportional to capacitance of sensor 120 as a function of increasing (up) and decreasing (down) external pressure exerted on the sensor, i.e., the graphical representation of the transfer function of the sensor.

EXAMPLE 3

Perforated Pad Saturated with Glycerin

FIG. 12A shows the variation of capacitance versus external pressure for a first variation 120A of the sensor 120 (Example 3) of FIGS. 3 and 4, in which the central perforated dielectric pad 130 thereof has a weight of about 1 gram and is saturated with 2 grams of glycerin.

EXAMPLE 4

Perforated Pad Saturated with Glycerin Doped with Iodine

FIG. 13A shows the variation of capacitance versus external force or pressure for a second variation 120b of sensor 120 (Example 4) shown in FIGS. 3 and 4, in which the central perforated dielectric pad 130 thereof is saturated with 1 gram of glycerin doped with 1 gram of a 2.5% solution of iodine in isopropyl alcohol.

EXAMPLE 5

Hybrid Piezocapacitive-Piezoresistive

FIGS. 5 and 6 illustrate an embodiment of a piezocapacitive-piezoresistive sensor 240 according to another aspect of the present invention. Sensor 240 has separate pressure sensing layers.

As shown in FIGS. 5 and 6, hybrid or composite piezocapacitive-piezoresistive sensor 240 includes a first pressure sensing layer consisting of a piezocapacitive section 250 which is substantially identical in construction and function to the modified sensor 120 shown in FIGS. 3 and 4. Piezocapacitance section 250 is similar to the first variation 120A of sensor 120 described above in which a central perforated foam dielectric pad 260 thereof is saturated with 2 grams of glycerin.

Referring to FIGS. 5 and 6, it may be seen that hybrid sensor 240 includes a second pressure sensing layer consisting of a piezoresistive section 280 which is positioned below piezocapacitive sensor section 250. However, the location of piezoresistive section 280 relative to piezocapacitive section 250 is not critical, and may optionally be positioned above the piezocapacitive section.

As shown in FIGS. 5 and 6, piezoresistive section 280 of hybrid sensor 240 has a laminated construction which is similar to that of piezocapacitive section 250. Thus, piezoresistive section 280 has a base conductive sheet 291 which consists of a thin, square sheet of conductive stretchy fabric which is substantially identical to upper conductive sheet 71 of sensor 50, and upper conductive sheet 271 of piezocapacitive section 250 of hybrid sensor 240. Piezoresistive section 280 includes an upper conductive sheet 311 which is substantially identical to base conductive sheet 251 of piezocapacitive sensor 250. Upper conductive sheet 311 of piezoresistive section 280 and base conductive sheet 251 of piezocapacitive section 250 comprise a single element 251-311.

Referring still to FIGS. 5 and 6, it may be seen that piezoresistive section 290 of hybrid sensor 240 includes a piezoresistive pad or core 390 which is supported on the upper surface 301 of base conductor sheet 291. As shown in the figures, piezoresistive pad 390 has the same outline shape and size, e.g., a two inch square, as base conductor sheet 291. In an example embodiment of sensor 240, piezoresistive pad 390 consists of a two inch square piece of type S8ZJJ polyurethane foam having a thickness of about 0.025 inch. The pad 390 is cut from a piece of unperforated foam which is impregnated with 2 grams of carbon lamp black having a particle size range of about 20 nm to about 40 nm.

FIG. 14 show the variation of voltage ratios V2/V1 measured at 30 KHz, proportional to admittance and hence capacitance, for increasing and decreasing pressure exerted on piezocapacitive section 150 of hybrid sensor 240, Example 5.

FIG. 15 show the variation of conductance measured at 10 KHz versus external pressure exerted on the piezocapacitive section 250 and piezoresistive section 280 of hybrid sensor 240, Example 5, measured for increasing and decreasing pressures.

EXAMPLE 6

Leaky Dielectric

Figure 8:
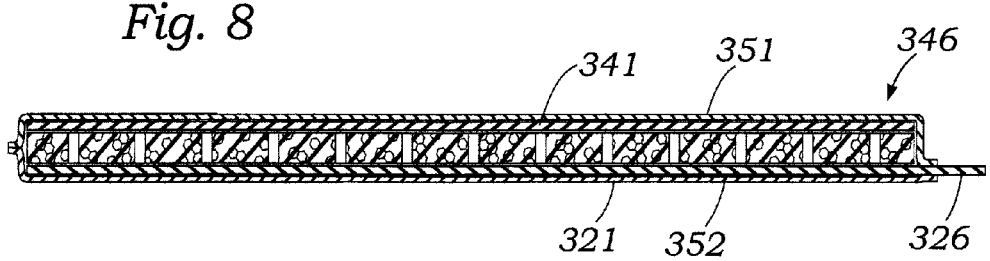
FIG. 8 is a vertical sectional view of the sensor of FIG. 7.

FIGS. 7 and 8 illustrate another embodiment 350 of a hybrid pressure sensor according to an aspect of the present invention. The embodiment 350 shown in FIGS. 7 and 8 is structurally similar to the embodiment 120 shown in FIGS. 3 and 4 and described above. However, embodiment 350 utilizes in place of the foam dielectric pad 130 a "leaky dielectric" pad 360.

In an example embodiment of the leaky dielectric piezocapacitive-piezoresistive pressure sensor 350, upper conductive sheet 341 and lower conductive sheet 321 are substantially identical to upper and lower conductive sheets 141, 121, respectively, of the embodiment 120 of a piezocapacitive sensor shown in FIGS. 3 and 4 and described above. The central dielectric pad 360 of sensor 350 has a composition and construction similar to that of un-perforated open-cell dielectric pad 60 of example 1 made of polyurethane foam shown in FIGS. 1 and 2. However, central dielectric pad 360 is treated to give it a piezoresistive characteristic in addition to a piezocapacitive characteristic by thoroughly mixing carbon black particles, of the type described above for example 5, with glycerin, and kneading the mixture of glycerin and carbon black particles into the foam pad.

FIG. 16 shows the variation of capacitance of leaky dielectric sensor 350 as a function of external pressure exerted on the sensor, measured at a relatively high frequency of 30KHz and thus displaying the capacitive part of the sensor transfer function FIG. 17 shows the variation of the conductance of leaky dielectric sensor 350 as a function of external pressure exerted on the sensor, measured at a relatively low frequency of 3 Hz and thus displaying the resistive part of the sensor transfer function.

FIG. 18 shows the variation of both capacitance and conductance of the leaky dielectric sensor 350 as a function of external pressure exerted on the sensor.

FIG. 19 shows the variation of the product of susceptance and conductance versus pressure transfer functions of the leaky dielectric sensor 350 as a function of external pressure exerted on the sensor. As may be seen by comparing FIG. 19 to FIG. 18, the product transfer function is substantially more linear and has substantially less hysteresis than either of the individual conductance or susceptance transfer functions.

EXAMPLE 7

Modification of Example 5, Hybrid Sensor with Paralleled Sections

FIG. 20 shows the variation of capacitance and conductance of a variation 240A of the sensor shown in FIGS. 5 and 6, in which the piezoresistive and piezocapacitive layers are electrically paralleled by connecting together their outer terminals 226, 296, as shown in hybrid configuration 2 of FIG. 9, to configure the sensor as a two terminal device, as a function of applied pressure for test frequencies of 30KHz and 3KHz.

EXAMPLE 8

Modification of Example 7 with Series Resistance

FIG. 21 shows the variation of capacitance and conductance with pressure for a modification 240B of the parallel two-terminal sensor configuration 240A, in which a 10,000 ohm resister is inserted in series with the sensor. As may be seen by comparing FIG. 21 with FIG. 20, the voltage versus pressure transfer function with a 10,000 ohm series resistance is substantially more linear and has substantially less hysteresis than the transfer function without a series resistance. Optionally a numerical value of a resistance such as 10,000 ohms may be inserted computationally in series in place of an actual resistance.

EXAMPLE 9

Figure 22:
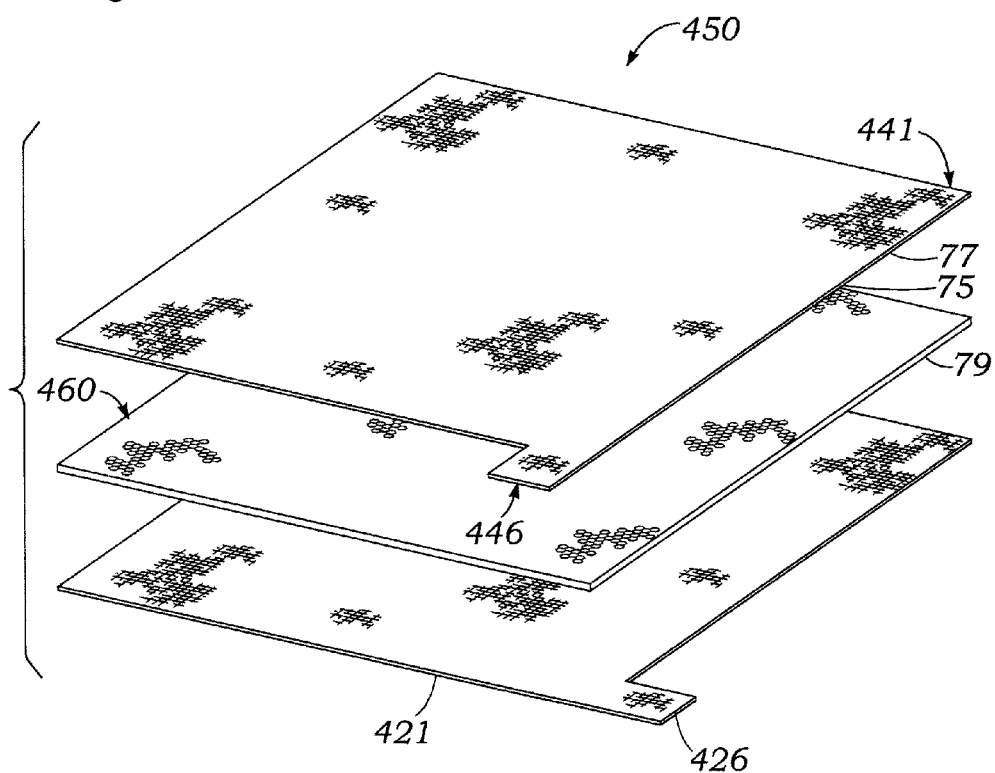
FIG. 22 is an exploded view of a modification of the fourth sensor embodiment of FIG. 7.
Figure 23:
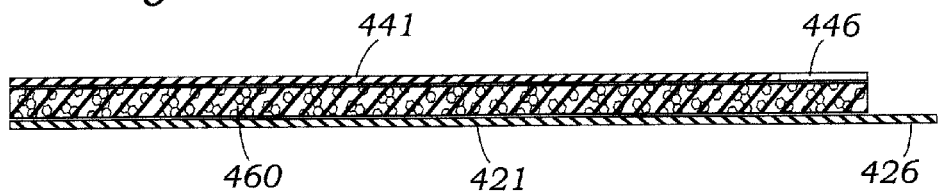
FIG. 23 is a vertical sectional view of the sensor of FIG. 22.

FIGS. 22 and 23 illustrate a simplified modification 450 of the leaky sensor 350 shown in FIGS. 7 and 8 and described above, in which the outer protective envelope is eliminated.

Figure 24:
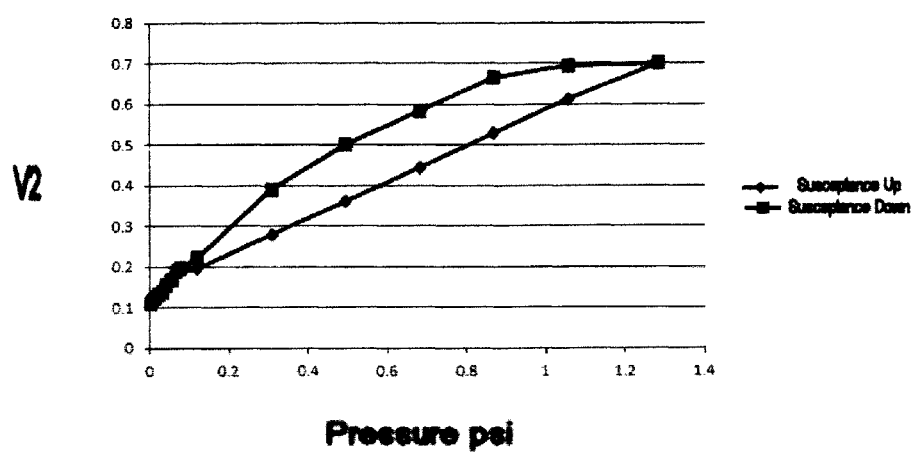
FIG. 24 is a graph showing capacitance versus applied pressure for the sensor of FIGS. 22 and 23, measured at 30KHz.

FIG. 24 is a graph showing the variation of capacitance of the simplified leaky sensor 450 as a function of increasing and decreasing pressures exerted on the sensor.

Figure 25:
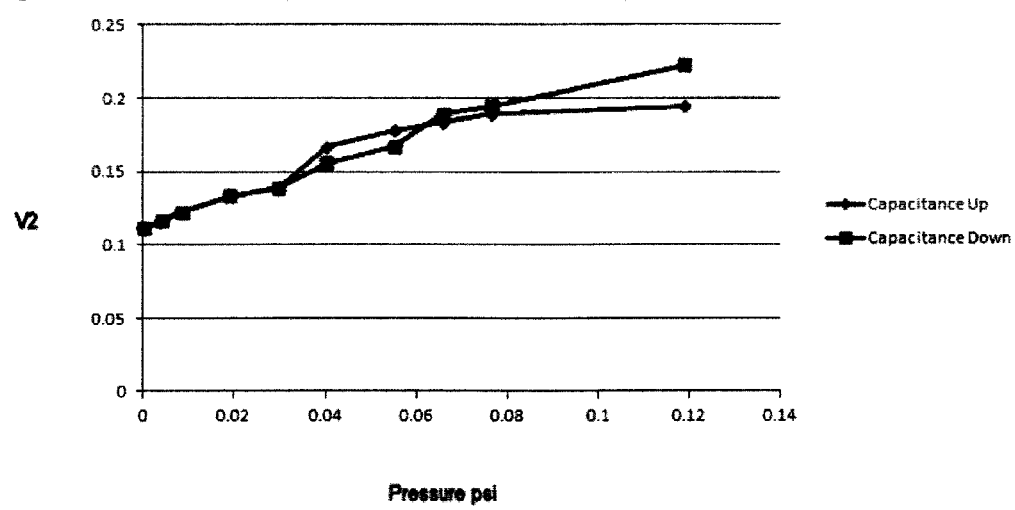
FIG. 25 is an expanded scale version of FIG. 24 showing capacitance versus pressure for a smaller range of pressures.

FIG. 25 is an expanded scale version of FIG. 24 showing capacitance versus pressure on sensor 450 for a smaller range of pressures.

Figure 26:
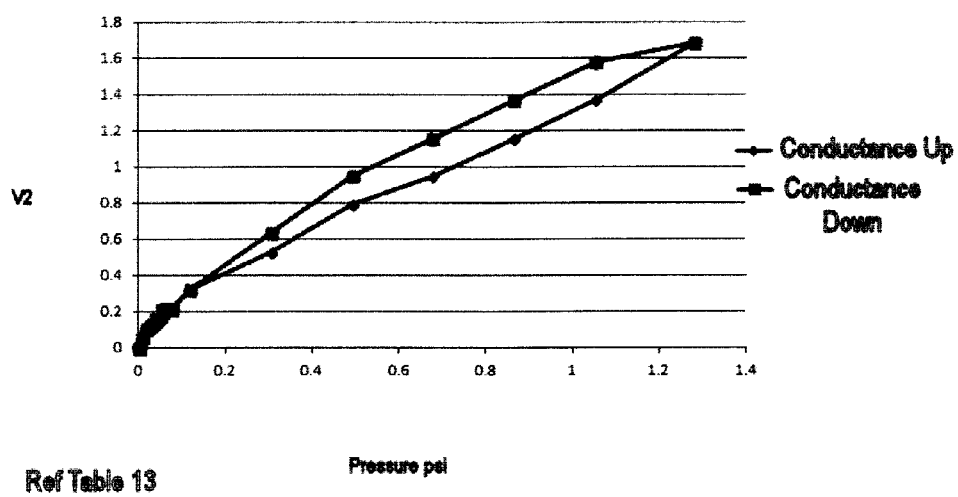
FIG. 26 is a plot of conductance versus increasing and decreasing pressure on the modified fourth sensor embodiment of FIGS. 22 and 23.

FIG. 26 is a plot of conductance versus increasing and decreasing pressures on the simplified leaky sensor 450.

Figure 27:
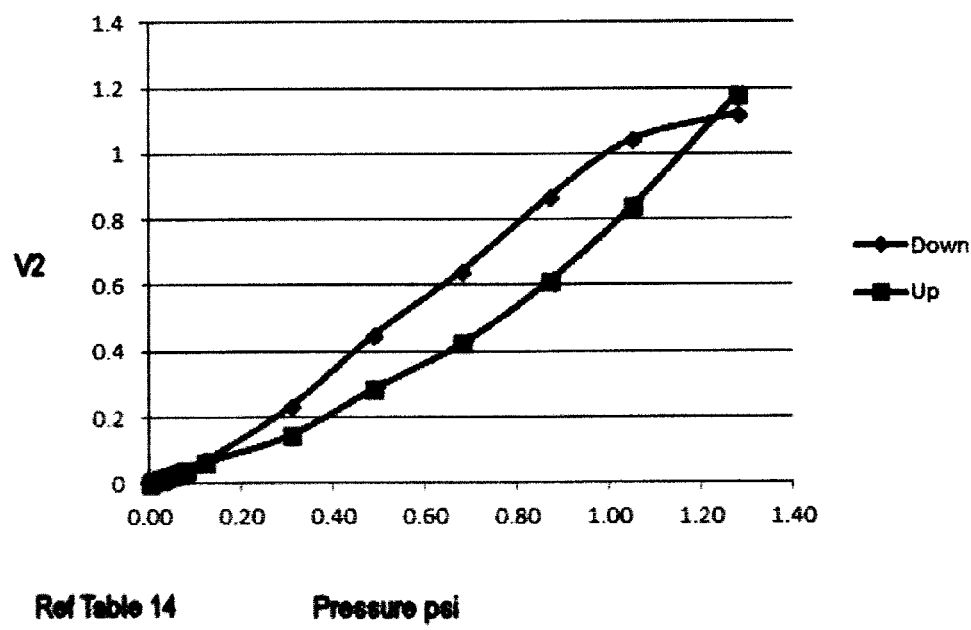
FIG. 27 is a plot of the multiplicative product of conductance and capacitance versus increasing and decreasing pressures on the modified fourth sensor embodiment of FIGS. 22 and 23.

FIG. 27 is a plot of the product of conductance times capacitance versus increasing and decreasing pressures on the simplified leaky sensor 450.

Pressure Sensing Mat

Figure 28:
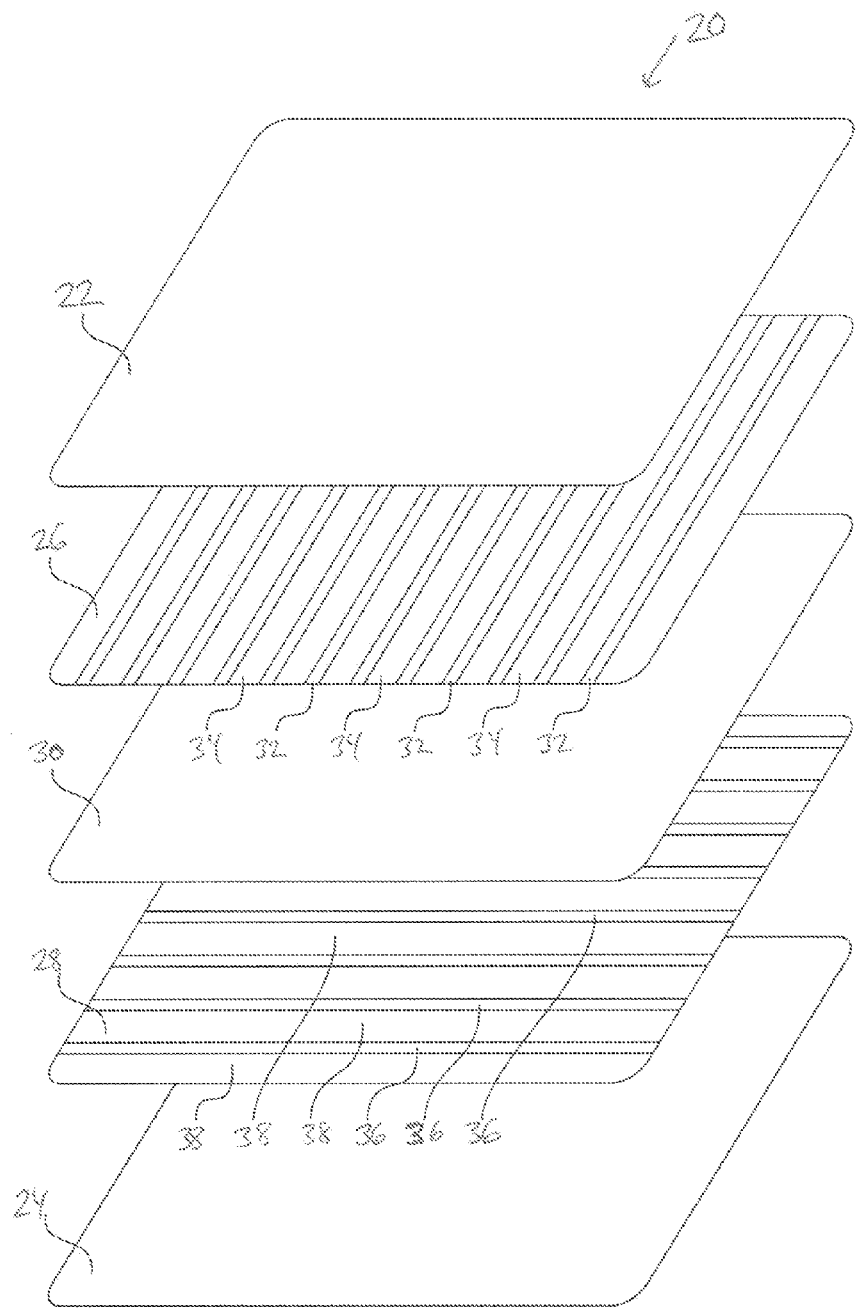
FIG. 28 is an exploded perspective view of one embodiment of a pressure sensing mat.

FIG. 28 shows one embodiment of a pressure sensing mat 20 according to another aspect of the present invention. Pressure sensing mat 20 is adapted for being positioned between a patient and a support surface on which a patient is positioned in order to detect the interface pressures between the patient and the patient support surface. Thus, for example, pressure sensing mat 20 may be used on the seat of a wheelchair, or on the top of a bed, stretcher, cot, operating table, or any type of furniture which a patient might lie or sit on (e.g. a recliner). When so used, mat 20 will customarily lie on top of the cushion, mattress, or other soft structure which is provided on the support surface. However, it is also possible for mat 20 to be integrated into the cushion, mattress, or other soft structure. However constructed, mat 20 detects a distribution of interface pressure between the support structure and those portions of the patient's body that are in contact with the support structure. This information can be used to help reduce any interface pressures that exceed a desired level, and thereby reduce the likelihood of bed sores developing.

In one embodiment, the outputs from pressure sensing mat 20 are used to control the inflation and deflation of one or more air bladders, or other inflatable structures, that are contained within the cushion, mattress, or other soft structure. The outputs are used to adjust the fluid pressures within the bladders so as to reduce the interface pressures in those areas where the interface pressure between the patient and the bladder(s) are relatively high. This helps spread the interface forces between the patient and the support surface over a greater area, thereby reducing the interface pressures and the likelihood of developing pressure sores. One manner in which a pressures sensing mat, such as pressure sensing mat 20, can be used to automatically adjust fluid pressures inside of an inflatable support structure is disclosed in U.S. patent application Ser. No. 12/075,937 filed on Mar. 15, 2008, by applicant Geoffrey Taylor and entitled ADAPTIVE CUSHION METHOD AND APPARATUS FOR MINIMIZING FORCE CONCENTRATIONS ON A HUMAN BODY, the complete disclosure of which is hereby incorporated herein by reference.

As illustrated in more detail, pressure sensing mat 20 includes a top cover 22, a bottom cover 24, an upper conductive layer 26, a lower conductive layer 28, and a central sensing layer 30. Top and bottom covers 22 and 24, respectively, made be made of the same material as cover sheets 81 and 82, described previously, or they may be made of other materials. In some embodiments, top cover 22 and bottom cover 24 are made from a waterproof material that is elastically stretchable. Such materials are available from Eastex Products of Holbrooke, Mass., or Dartex Coatings of Nottingham, United Kingdom. Top cover 22 and bottom cover 24 are sealed together about their periphery to thereby envelope layers 26, 28, and 30. Electrically conductive leads, however, pierce this seal in order to provide electrical communication to the conductive layers 26 and 28, as well as the sensing layer 30, as will be discussed in greater detail below.

In one embodiment, sensing layer 30 is a leaky dielectric pad that is the same as leaky dielectric pad 360 described above. Upper conductive layer 26 includes a plurality of nonconductive columns 32 that are alternately separated by a plurality of conductive columns 34. Lower conductive layer 28 includes a plurality of nonconductive rows 36 that are alternately separated by a plurality of conductive rows 38. The manner in which upper and lower conductive sheets 26 and 28 are constructed is described in more detail in U.S. patent application Ser. No. 13/644,961 filed Oct. 4, 2012 by applicant Geoffrey Taylor and entitled PRESSURE SENSING MAT, the complete disclosure of which is also hereby incorporated herein by reference. When so constructed, upper and lower conductive sheets 26 and 28 are elastically stretchable and capable of carrying electrical signals along their respective conductive columns 34 and conductive rows 38.

Figure 29:
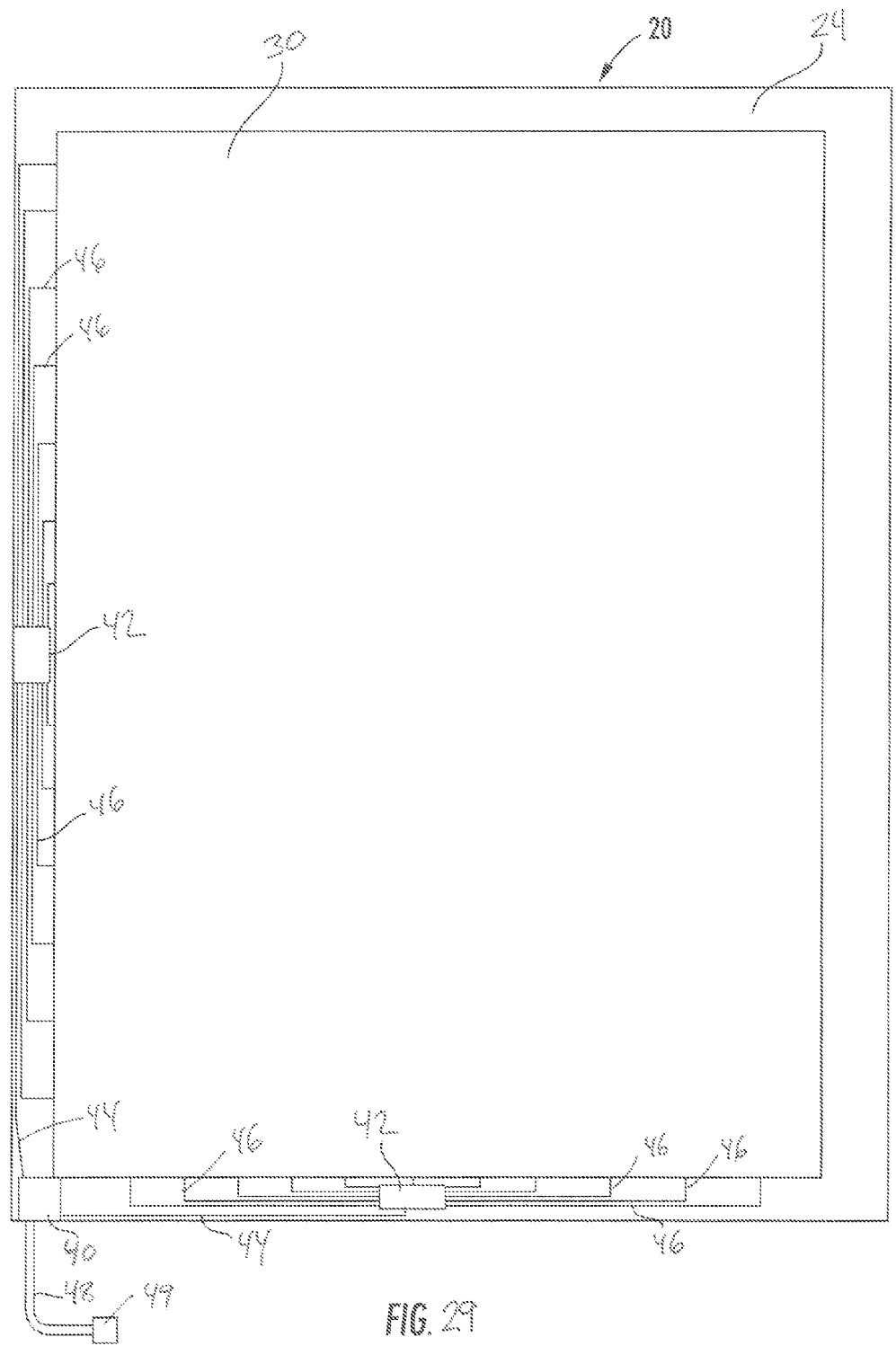
FIG. 29 is a plan view of the pressure sensing mat of FIG. 28 shown with a top cover and upper conductive layer removed.

FIG. 29 illustrates a plan view of pressure sensing mat 20 shown with top cover 22 and upper conductive layer 26 removed, wherein the electrical components and circuitry used to read and process the electrical outputs at each intersection of the conductive columns 34 with conductive rows 38. Each such intersection defines, in essence, an individual pressure sensor. The product of the number of conductive columns 34 and conductive rows 38 therefore defines how many individual pressure sensors pressure sensing mat 20 is capable of having. When pressure is exerted by a patient on sensing mat 20, this is detected by the change in the corresponding electrical characteristics of the sensors in the area where the pressure changed. As was described above, the magnitude of external pressures exerted on each of the sensors can be accurately determined by measuring the conductance of each sensor using an applied DC voltage or a low frequency alternating current test signal having a frequency of, for example, 1 Hz to 30 Hz, while the capacitance of each individual sensor can be measured by applying a higher frequency alternating current test voltage or current of, for example, 30KHz. Moreover, combinations of DC or low frequency test voltages or currents may be applied to each sensor simultaneously or sequentially with higher frequency test voltages or currents to determine the interface pressure exerted on the sensor.

As shown in FIG. 29, a controller 40 carries out the electrical processing necessary to read the susceptance and conductance of each individual sensor. Controller 40 is in electrical communication with a pair of communication links 44. Each communication link 44 communicatively couples controller 40 with a preprocessing circuit boards 46. Such links may utilize any suitable form of communication, such as a serial connection, a parallel connection, or another type of connection. In one embodiment, the communication links 44 follow the I squared C protocol. Other protocols, such as, but not limited to, CAN, LIN, and others may be used.

Each preprocessing circuit board 42 is in electrical communication with a plurality of wires or conductors 46. Wires or conductors 46 are each in electrical communication with an individual one of conductive columns 34 or of conductive rows 38. Controller 40 communicates with preprocessing circuit boards 42 to send signals to individual ones of the sensors defined in mat 20 and monitor the response to those signals. Controller 40 accomplishes this by picking the specific row conductor 38 and specific column conductor 34 whose intersection defines the sensor desired to be read. Controller 40 then uses the preprocessing circuit boards 42 to measure the susceptance and conductance at that chosen sensor. These readings are stored in a memory accessible to controller 40, which may either be contained within controller 40, or which may be in communication with controller 40 via a cable 48. Cable 48 includes a connector 49 that enables it to be connected to an appropriate consumer of the information generated by controller 40. In one embodiment connector 49 is a USB connector. Other types of connectors may be used.

In some embodiments, as was noted previously, the consumer of the data generated by controller 40 may be a mattress. In other embodiments, connector 49 is plugged into a personal computer, laptop computer, or tablet computer, and the data generated by controller 40 is able to be stored and/or further processed by the attached computer. Regardless of the consumer, controller 40 is configured to monitor the capacitance and susceptance of each individual sensor multiple times a second. The data from the results of these measurements can be used to create a graphical display of patient interface pressures that are spatially distributed over the area of the pressure mat 20.

In one embodiment, controller 40 is enveloped within top and bottom covers 22 and 24 so that controller 40 is not visible to a user of mat 20. Further, both circuit boards 42 may be each less than half an inch thick (such as, for example, 2 millimeters), and each may take up less than a square inch of surface area. Such dimensions help to ensure that a patient will not likely be able to feel these circuit boards within mat 20, and thus will not be discomforted by them. This is especially true if the circuit boards 42 and controller 40 are positioned along the edges of the sensing mat 30. Controller 40 may be positioned in a corner at a foot end of the sensing mat 20 in order to reduce the likelihood of it being felt by a patient.

Still further, in some embodiments, controller 40 and preprocessing boards 42 are manufactured from flexible electronics, commonly known as flex circuits. Such flexible electronics are mounted to a flexible plastic substrate, such as, but not limited to, a polyimide, a polyether ether ketone (PEEK), or a conductive polyester film. By using flexible electronics, controller 40 and preprocessing boards 42 are able to physically bend, thereby helping to protect them against breakage and also reducing any discomfort they might otherwise cause to a patient.

Controller 40 may be a conventional commercially available microcontroller, microprocessor, or other programmable device, that is programmed to carry out the functions described herein. Controller 40 includes, in some embodiments, the circuitry of FIG. 9, as well as any additional components necessary for reading the voltages, resistance, and other electrical characteristics described with respect to FIG. 9. When pressure sensing mat 20 utilizes a single leaky dielectric layer 30 that is the same as dielectric pad 360, controller 40 is configured to implement the same functions as the test circuitry of FIG. 9 that corresponds to the "piezocapacitive and leaky test configuration," rather than the "piezocapacitive and piezoresistive hybrid configurations" (either #1 or #2).

However, it will be understood by those skilled in the art that pressure sensing mat 20 can be modified to include a separate piezocapacitive layer and a separate piezoresistive layer. When such separate layers are included, an additional conductive layer having either conductive rows 38 or conductive columns 34 is added to the mat. Such a mat will therefore include, inside covers 22 and 24, a bottom conductive layer (either rows or columns), a piezocapacitive layer on top of the bottom conductive layer, a middle conductive layer (either rows or columns, but opposite of the bottom conductive layer), a piezoresistive layer on top of the middle conductive layer, and a top conductive layer (either rows or columns, but the same as bottom conductive layer). Of course, the position of the piezoresistive and piezocapacitive layers can be reversed, if desired.

In another alternative embodiment (not shown), instead of utilizing a single sensing layer 34 made of the same material as dielectric pad 360, pressure sensing mat 20 includes a sensing layer 34 made of a plurality of individual squares (or other shapes) of dielectric pads 360, wherein each square is positioned at an intersection of a row conductor 38 and a column conductor 34. Each square dielectric pad 360 is spaced apart from its neighboring dielectric pads 360 so that the pads are electrically isolated from each other. Such spacing may be filled by any suitable electrically insulating material that is flexible, and in some embodiments, elastically stretchable. Alternatively, the spacing may be left empty, and each individual pad 360 may be fixed in position by alternative means, such as by adhesive, stitching, or other means. Regardless of the manner of affixing pads 360 in position, only the dielectric pad 360 corresponding to an individual sensor will be in electrical series between the conductive row and conductive column corresponding to that sensor. This contrasts with the embodiment of mat 20 shown in FIG. 28 where the entire sensing layer 34 is effectively in electrical series between the corresponding conductive row and conductive column.

When mat 20 is made of an array of hybrid sensors that vary in capacitance and conductance in response to external pressures exerted on the sensors, the mat provide significant advantages over pressure sensing mats that vary with respect to only capacitance, or with respect to only conductance. For example, response time to pressure impulses and linear dynamic range regions, among other parameters, vary differently for the conductive and capacitive sections of the hybrid sensors. These variations enable adaptive optimization of sensor accuracy, repeatability, and response time by judicious choices of combinations of the frequencies of voltages or currents used to sample the individual sensors. Further, the sensing of dual electrical properties (e.g. capacitance and resistance) enables flexible pressure sensing mats to be constructed that have a wider dynamic range than mats that measure only a single electrical property.

The above description is that of several embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construe

What is claimed is:

1. A flexible force sensing mat comprising:
   a first sheet having a plurality of first conductive paths supported thereon;
   a layer of sensing material positioned in contact with said first conductive paths, said layer of sensing material having first and second electrical characteristics that vary in response to physical forces exerted thereon;
   a second sheet positioned in contact with said layer of sensing material on a side of said layer of sensing material opposite said first sheet, said second sheet having a plurality of second conductive paths supported thereon, said plurality of second conductive paths being transverse to said plurality of first conductive paths; and
   a controller adapted to detect changes in both said first and second electrical characteristics when force is applied to said force sensing mat.

2. The mat of claim 1 wherein said first sheet, said second sheet, and said layer of sensing material are all elastically stretchable.

3. The mat of claim 2 wherein said first and second sheets are made of nylon.

4. The mat of claim 3 wherein said first conductive paths and said second conductive paths are defined by metal plated to said first and second sheets, respectively.

5. The mat of claim 1 wherein said first electrical characteristic is capacitance and said second electrical characteristic is resistance.

6. The mat of claim 1 wherein said controller detects changes in said first electrical characteristic by feeding a first electrical signal to a selected one of said first or second conductive paths, and said controller detects changes in said second electrical characteristic by feeding a second electrical signal to said selected one of said first and second conductive paths, said first electrical signal having a different frequency than said second electrical signal.

7. The mat of claim 6 wherein said first electrical characteristic is capacitance and said second electrical characteristic is resistance.

8. The mat of claim 7 wherein said layer of sensing material includes carbon black and glycerin mixed together.

9. The mat of claim 8 wherein said carbon black and glycerin are supported in a foam pad positioned between said first and second sheets.

10. A flexible force sensing mat comprising:
    a first sheet having a plurality of first conductive paths supported thereon;
    a first layer of sensing material positioned in contact with said first conductive paths, said layer of sensing material having a first electrical characteristic that varies in response to physical forces exerted thereon;
    a second sheet having a plurality of second conductive paths supported thereon, said second sheet positioned in contact with said first layer of sensing material on a side of said layer of sensing material opposite said first sheet;
    a second layer of sensing material positioned in contact with said plurality of second conductive paths, said second layer of sensing material having a second electrical characteristic that varies in response to physical forces exerted thereon, said second electrical characteristic being different from said first electrical characteristic; and
    a third sheet having a plurality of third conductive paths supported thereon, said third sheet positioned in contact with said second layer of sensing material on a side of said second layer of sensing material opposite said second sheet.

11. The mat of claim 10 further including a controller in electrical communication with said first, second, and third conductive paths, said controller adapted to detect changes in both said first and second electrical characteristics when force is applied to said force sensing mat.

12. The mat of claim 11 wherein said first electrical characteristic is capacitance and said second electrical characteristic is resistance.

13. The mat of claim 12 wherein said controller detects changes in said first electrical characteristic by feeding a first electrical signal to a selected one of said first or second conductive paths, and said controller detects changes in said second electrical characteristic by feeding a second electrical signal to said selected one of said first and second conductive paths, said first electrical signal having a different frequency than said second electrical signal.

14. The mat of claim 13 wherein said first sheet, said second sheet, said third sheet, and said first and second layers of sensing material are all elastically stretchable.

15. The mat of claim 14 wherein said first, second, and third sheets are all made of nylon.

16. The mat of claim 15 wherein said first, second, and third conductive paths are defined by silver plated to said first, second, and third sheets, respectively.

17. The mat of claim 10 wherein said first sheet, said second sheet, said third sheet, and said first and second layers of sensing material are all elastically stretchable.

18. The mat of claim 17 wherein said first electrical characteristic is capacitance and said second electrical characteristic is resistance.

19. The mat of claim 10 wherein said first, second, and third sheets are all made of nylon.

20. The mat of claim 19 wherein said first, second, and third conductive paths are defined by metal plated to said first, second, and third sheets, respectively.

* * * * *